US012478965B2

(12) United States Patent
Lee et al.

(10) Patent No.: US 12,478,965 B2
(45) **Date of Patent: *Nov. 25, 2025**

(54) CAVITY ACOUSTIC TRANSDUCER (CAT) FOR SHEAR-INDUCED CELL TRANSFECTION

(71) Applicant: THE REGENTS OF THE UNIVERSITY OF CALIFORNIA, Oakland, CA (US)

(72) Inventors: Abraham P. Lee, Irvine, CA (US); Mohammad Aghaamoo, Irvine, CA (US); Xuan Li, Irvine, CA (US); Neha Garg, Irvine, CA (US); Yu-Hsi Chen, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1189 days.

This patent is subject to a terminal disclaimer.

(21) Appl. No.: 17/340,581

(22) Filed: Jun. 7, 2021

(65) Prior Publication Data

US 2021/0291185 A1 Sep. 23, 2021

Related U.S. Application Data

(63) Continuation-in-part of application No. 16/547,152, filed on Aug. 21, 2019, now Pat. No. 11,052,395.

(60) Provisional application No. 62/720,829, filed on Aug. 21, 2018.

(51) Int. Cl.

*B01L 3/00* (2006.01)
*C12N 15/87* (2006.01)

(52) U.S. Cl.

CPC ... *B01L 3/502761* (2013.01); *B01L 3/502715* (2013.01); *B01L 3/50273* (2013.01); *B01L 3/502769* (2013.01); *C12N 15/87* (2013.01); *B01L 2200/0668* (2013.01); *B01L 2200/18* (2013.01); *B01L 2300/0645* (2013.01); *B01L 2300/0809* (2013.01); *B01L 2400/0415* (2013.01); *B01L 2400/0436* (2013.01); *B01L 2400/0439* (2013.01)

(58) Field of Classification Search

CPC ......... B01L 3/502761; B01L 3/502715; B01L 3/50273; B01L 3/502769; B01L 2200/0668; B01L 2200/18; B01L 2300/0645; B01L 2300/0809; B01L 2400/0415; B01L 2400/0436; B01L 2400/0439; C12N 15/87; C12M 23/16; C12M 35/00; C12M 35/04

See application file for complete search history.

(56) References Cited

U.S. PATENT DOCUMENTS

| | | | |
|---|---|---|---|
| 9,517,465 B2 | 12/2016 | Patel et al. | |
| 11,052,395 B2 * | 7/2021 | Lee | C12N 15/87 |
| 2018/0016539 A1 | 1/2018 | Ding et al. | |

FOREIGN PATENT DOCUMENTS

| | | |
|---|---|---|
| WO | WO2016077761 A1 | 5/2016 |

OTHER PUBLICATIONS

Tovar et al. "Lateral cavity acoustic transducer." Twelfth International Conference on Miniaturized Systems for Chemistry and Life Sciences Oct. 12-16, 2008, San Diego, California, USA. 1384-1386.

Garg, N. et al. Whole-Blood Sorting. Enrichment and in situ Immunolabeling of Cellular Subsets Using Acoustic Microstreaming. Microsystems & Nanoengineering. Feb. 26, 2018, vol. 4.17085. DOI:10.1038/micronano.2017.85.

Nivedita et al., A high throughput microfluidic platform for size-selective enrichment of cell populations in tissue and blood samples, 2017, Ananlyst, 2558-2569 (Year: 2017).

* cited by examiner

*Primary Examiner* — Narayan K Bhat
(74) *Attorney, Agent, or Firm* — NGUYEN TARBET IP LAW

(57) ABSTRACT

The present invention features the use of cavity acoustic transducers (CATs) to apply mechanical stimuli on cells. CATs utilize the generated acoustic microstreaming vortices to trap cells and apply tunable shear on them. The present invention may use such a portable, automated, and high throughput device for cell transfection.

20 Claims, 19 Drawing Sheets

CAVITY ACOUSTIC TRANSDUCER (CAT) FOR SHEAR-INDUCED CELL TRANSFECTION

CROSS-REFERENCES TO RELATED APPLICATIONS

This application is a continuation-in-part and claims benefit of U.S. Non-Provisional patent application Ser. No. 16/547,152, filed Aug. 21, 2019 which claims benefit of U.S. Provisional Patent Application No. 62/720,829, filed Aug. 21, 2018, the specifications of which are incorporated herein in their entirety by reference.

GOVERNMENT SUPPORT

This invention was made with Government support under Grant No. IIP-1538813, awarded by the National Science Foundation. The Government has certain rights in the invention.

FIELD OF THE INVENTION

The present invention relates to devices and methods for intracellular delivery of exogenous materials. More specifically, the present invention relates to devices and methods for cell transfection.

BACKGROUND OF THE INVENTION

Intracellular delivery of exogenous materials is an essential tool for gene therapy, the delivery of nucleic acids into cells to correct aberrant genes or for genetic engineering of cells that can be used for cellular therapy (e.g. CAR T cell therapy or stem cell therapy). Although several methods have been developed for cell transfection such as the use of viral and non-viral vectors, electroporation, cell membrane's rapid mechanical disruption, etc., the field still faces several challenges. Risk of disrupting the vital parts of the host cell genome in methods that use viral vectors, low transfection efficiency in methods that use non-viral vectors, and high cell death rate in electroporation are among the shortcomings of the existing methods. In addition, most current devices are not portable and lack the capability to be automated, tunable, and integrated with other platforms.

Mechanical stimuli are among the key factors affecting cell behavior. For many years, biologists and biomedical engineers have applied mechanical stimuli on cells to study their biological responses such as growth, gene expression, intracellular uptake, etc. In recent years, there has been growing interest in the use of microfluidics technology to apply mechanical stimuli on single cell level and with precise and high throughput manner. Although so many promising microfluidics methods have been developed for this purpose, the field still needs further improvement as the current methods are either low throughput or suffer from high complexity.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

To address the current limitations for intracellular delivery of exogenous materials, the present invention features a portable device platform, with no external pump required, based on cavity acoustic transducers (CATs), for cell transfection based on shear-induced cellular deformation or electroporation. The CATs are designed to apply tunable shear stress and, in some embodiments, shear-induced cell deformation on single cells. The oscillating interface in CATs results in acoustic microstreaming vortices in the device. The cells that are trapped in these vortices experience shear stresses that can be varied by the changes in the interface oscillation controlled by the piezoelectric transducer (PZT) voltage. In addition, the slanted angle of CATs may provide the device with pumping the bulk flow that eliminates the need for external pumping. The present invention demonstrates the use of CAT for cell transfection. By applying mechanical stimuli on cells, CAT can deform a cell membrane and make it permeable to exogenous materials.

Cavity Acoustic Transducers (CATs) are an array of acoustically actuated interfaces generated using dead-end channels. The oscillating interface in CATs may result in acoustic microstreaming vortices in the device. The cells that are trapped in these vortices may experience shear stresses that can be varied by the changes in the interface oscillation controlled by the piezoelectric transducer (PZT) voltage. As a result of the shear stresses experienced by the cells, they may undergo mechanical deformation. The mechanical deformation of cells may create transient membrane disruptions or transient holes in their membranes that may facilitate delivery of exogenous materials into the cells. According to the preliminary results, the present invention demonstrates successful intracellular delivery of 70 kDa dextran molecules into the cells. Much larger or smaller molecules may also be transfected using the device of the present invention. In addition, the slanted angle of the CATs of the present invention may provide the device with pumping the bulk flow that may eliminate the need for external pumping and also provide steady supply of the exogenous materials as the cells are trapped in vortices. This feature may make the CATs of the present invention an ideal portable platform for cell transfection. Another advantage of the present invention is the ability to deliver the exogenous material into the cell uniformly and in bulk, while being able to tune the size of the nanopores at the same time. It is believed that no other microfluidic transfection method combines all these advantages and still has relatively high throughput.

Compared to existing transfection methods, the present invention can not only deliver a wide range of molecular sizes at high efficiency, but also offers unique sample processing advantages. For example, the unique design of Cavity Acoustic Transducers (CATs) generates a bulk flow that eliminates the need of external pumping. In addition, the presented platform is capable of size-based selective transfection. This unique feature is highly desirable for applications where transfection of specific cellular population is targeted. Furthermore, since cells may be trapped and suspended in microstreaming vortices, the microfluidic channels may be wider than in other microfluidic transfection devices, thus making them higher throughput and less clog-prone. Contrastingly, the other microfluidic transfection devices typically flow cells one-by-one and have channel dimensions at the scale of single cells.

Furthermore, the devices and methods of the present invention may use a combination of CAT generated mechanical deformation and electroporation in order to provide for high delivery efficiency transfection. This combination may provide better results for transfection than either of the two individual approaches. As a non-limiting example, the combination may allow for very gentle, high throughput transfection of large molecules into cells of a certain size. The microstreaming vortices generated by oscillation of the CATs may be used to simultaneously trap cells of a certain size and gently create initial pores via mechanical deformation, while also pumping a fluid so as to separate the desired cells from cells of a different size. This approach is more gentle than previous transfection strategies because of the lower, more uniform shear stress applied on the cells. Gentleness is defined for a given shear stress limit, that all cells experience the same uniform shear stress as they 'tumble' in the vortices. In other high-throughput transfection devices, the bandwidth of shear stress is large such that to hit a certain shear stress level means some of the cell population will experience much higher shear stress and result in membrane disruption and high probability of deteriorated cell viability. The present invention provides for a more uniform, narrow-bandwidth of shear stress.

Electroporation of these selected cells could then gently expand the pores to promote transfection. Since CAT fluid-induced mechanical deformation and electroporation are applied to cells simultaneously, they help each other to be applied in a more gentle manner individually. This is in contrast to conventional solid barrier-induced mechanical deformation methods where the cells experience very high shear stress and mechanical deformation induced by constrictions smaller than size of the cells or high hydrodynamic flows. Thus, the shear stresses generated by the present invention may be much lower and more widely distributed across the cellular surface than the higher, more focused stresses of other transfection devices. Unlike other transfection strategies, since cells are trapped and suspended in microstreaming vortices, the microfluidic channels are wider, and the number of CATs can be easily scaled up, this approach may be done in a high throughput manner. For example, one embodiment of the present invention provides a throughput of about 3.6 million cells per hour (60,000 cells per minute). Ease of scaling up of the CATs provides the potential capability to increase the throughput without adding complexity to the system.

One of the unique and inventive technical features of the present invention is that the CAT devices may provide a simple way to apply wide ranges of shear stresses and shear-induced deformation on cells. As a non-limiting example, the shear stress may be about 30-45 Pa, or below about 50 Pa. Without wishing to limit the invention to any theory or mechanism, it is believed that the technical feature of the present invention advantageously provides for subjecting the cells to mechanical stimuli for any duration without physically trapping the cells or passing them through a very long microchannel. Also, the shear stress may be uniformly applied such that more cells are appropriately stressed for the size of the exogenous materials to be delivered. Higher shear stress is required for larger delivery molecules, but without the stress uniformity provided by the present invention, subpopulations of cells would experience much higher stresses and could result in membrane disruption. Additionally, the device can be automated with multiplexed delivery of cells and transfection reagents. Furthermore, the CAT can itself be a sample preparation for only transfecting subpopulations of cells with size thresholds and potentially deformability thresholds. None of the presently known prior references or work has the unique inventive technical feature of the present invention.

An additional advantage of the present system is that it allows for higher uniformity of transfection than previous approaches. In other words, each cell is transfected with approximately the same number of transfected molecules. Without wishing to limit the present invention to any particular theory or mechanism, it is believed that the same microstreaming vortices which are responsible for mechanical deformation of the cells also provide for a mixing of the fluid which contains both the cells and the material to be transfected. While other systems rely on diffusion to mix the cells and the exogenous material, this mixing may provide for a more uniform distribution and thus a more uniform transfection. Without wishing to limit the present invention to any particular theory or mechanism, it is believed that the mixing caused by the microstreaming vortexes may be a key factor which contributes to the increased efficiency of transfection. As a non-limiting example, present invention may provide for a high proportion of the transfected cells with at least 50% delivery of the molecules. In this regard, the present invention may be at least an order of magnitude better than electroporation alone.

BRIEF DESCRIPTION OF THE DRAWINGS

The features and advantages of the present invention will become apparent from a consideration of the following detailed description presented in connection with the accompanying drawings in which:

FIG. 11A shows a histogram plot which illustrates a significant shift in fluorescence intensity of the experimental group (delivery using a CAT device) from the control group. FIG. 11B shows a quantification graph of the results, where the CAT device provides 80% delivery efficiency of 3-KDa dextran.

FIG. 12A shows a histogram plot which illustrates the use of a CAT device integrated with on-chip electroporation (EP) (short AC electric field pulses with 10V applied voltage and 10 KHz frequency) results in a significant shift in fluorescence intensity of cells compared to the control group and to the group treated by the CAT device alone. FIG. 12B shows a quantification graph of the results, where integration of the CAT device with on-chip electroporation shows high delivery efficiency of 45% compared to the CAT device alone (15%) and control (4%) groups.

DESCRIPTION OF PREFERRED EMBODIMENTS

Figure 1:
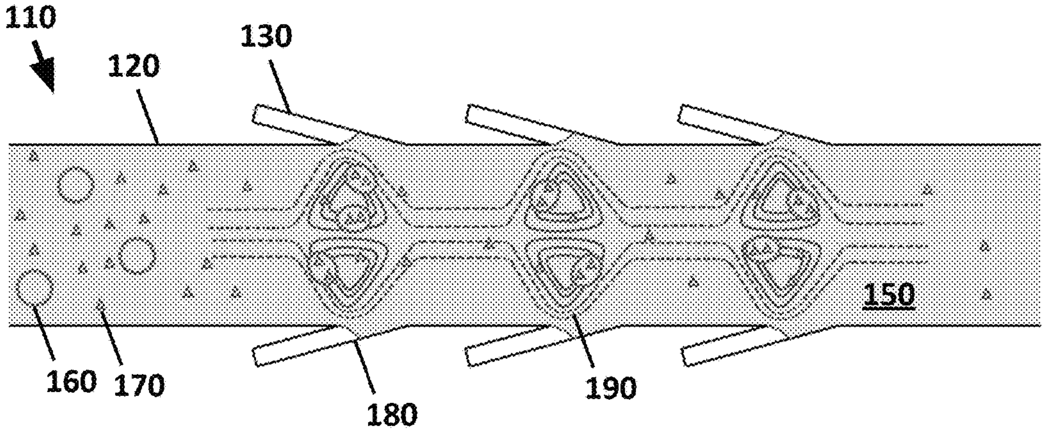
FIG. 1 shows a schematic of a CAT for cell transfection.
Figure 2:
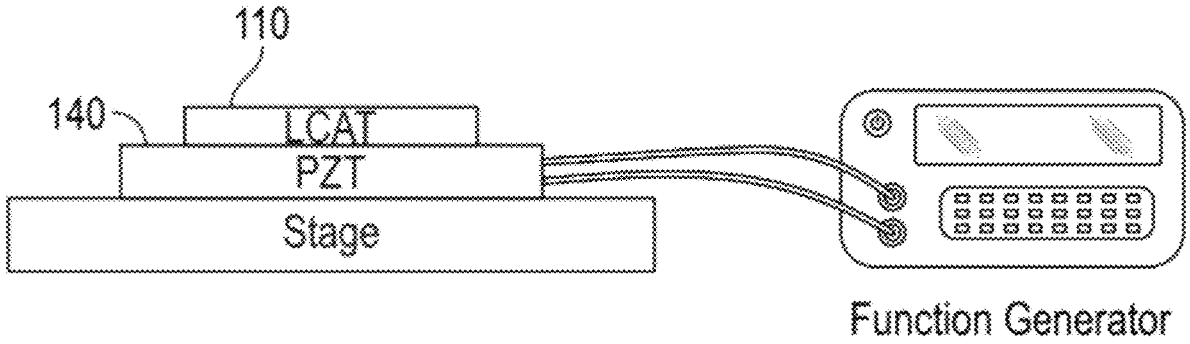
FIG. 2 shows a schematic drawing of the device setup for a CAT device of the present invention.
Figure 3A:
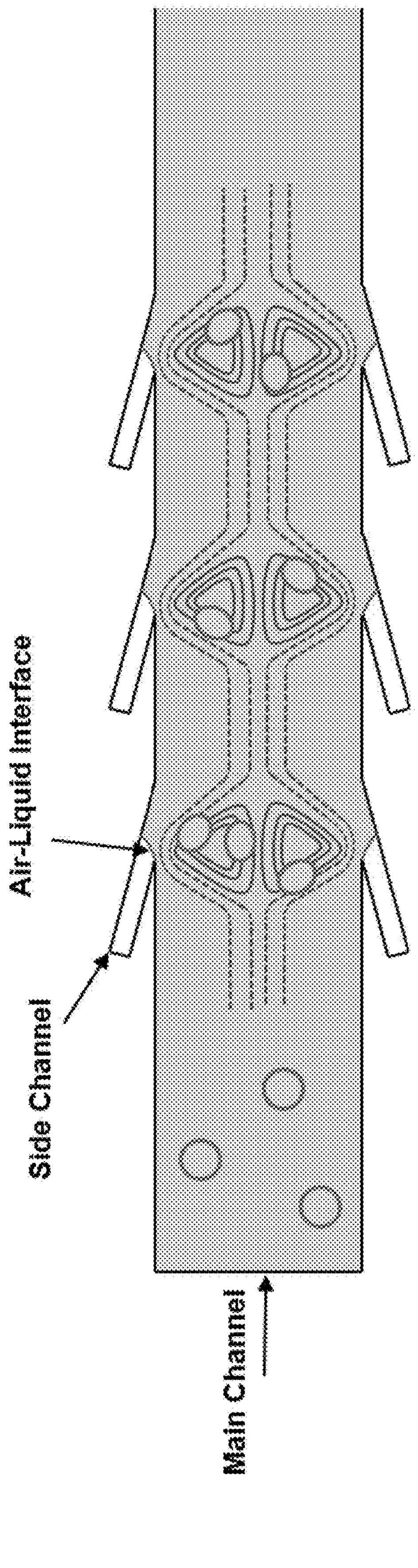
FIG. 3A shows a schematic of a CAT device having a main channel, a plurality of channels, and a plurality of interfaces.
Figure 3B:
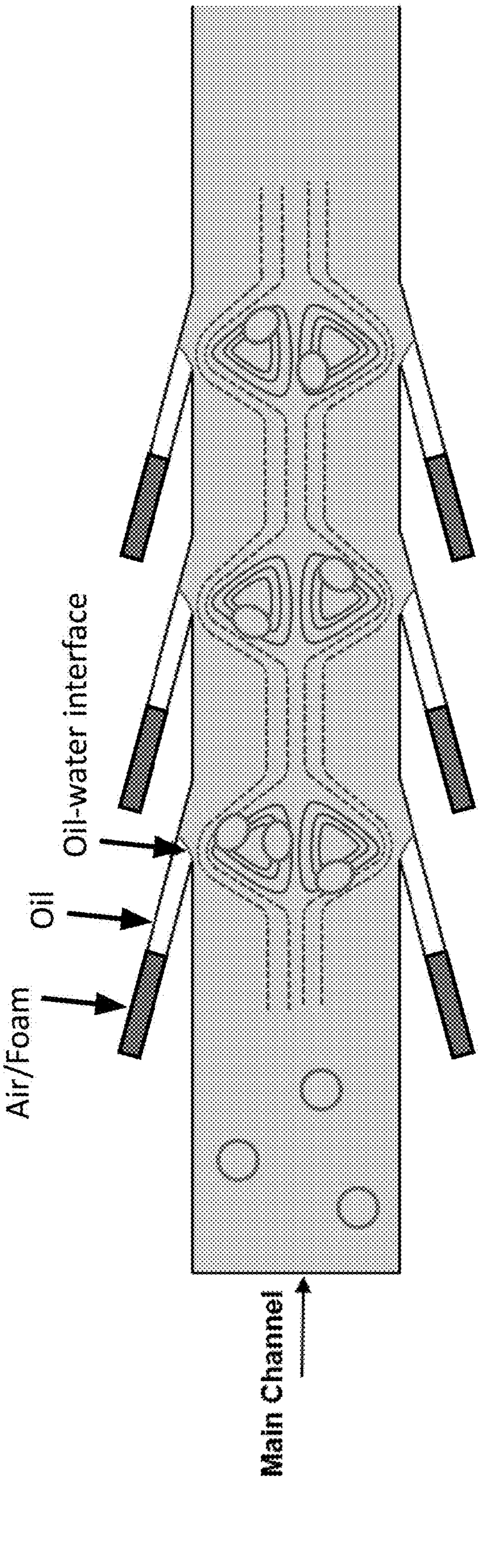
FIG. 3B shows a schematic of a CAT device having a main channel, a plurality of channels which are partially filled with air or foam and capped by an oil plug, and a plurality of oil-water interfaces.

Following is a list of elements corresponding to a particular element referred to herein:

100 microfluidic system
110 microfluidic platform
120 main microfluidic channel
130 CAT
140 acoustic source
150 fluid
160 cell
170 exogenous material
180 interface
190 microstreaming vortices
200 electrode As used herein, "exogenous material" refers to a substance, compound, polymer, or material which is outside of a cell. As a non-limiting example, an exogenous material may be a drug, a prodrug, an indicator, a dye, a fluorescent tag, a protein, a biomaterial, a polymer, a small molecule, a transfection molecule, or a compound which is outside of a cell. An exogenous material may be delivered into the interior of a cell for a variety of reasons including but not limited to molecular biology research, genetic therapy, medicine, therapeutic treatment of the cell, modification of the cell, or labelling of the cell.

As used herein, "electroporation" refers to a process of applying a voltage to one or more cells. Without wishing to limit the present invention to a particular theory or mechanism, electroporation can generate pores in the membrane of the one or more cells in order to allow the delivery of exogenous materials into the one or more cells. Electroporation can also widen the size of pre-existing pores, and/or the generated pores, in the membrane of the one or more cells in order to allow more consistent delivery of exogenous material and/or delivery of larger exogenous material into the one or more cells. In some embodiments, the one or more cells may experience shear prior to electroporation.

As used herein, Cavity Acoustic Transducers (CATs) are simple on-chip actuators that are easily fabricated and can be actuated using a battery operated portable electronics platform. CATs are dead-end channels that are in the same plane laterally or vertically with respect to the microchannels. In some embodiments, the CATs require no additional fabrication steps other than those needed to produce a single layer or multilayer device. When the device is filled with liquid, CATs trap bubbles creating an interface that can be excited using an external acoustic source such as a piezoelectric transducer. The interface generated by a CAT may be selected from a group comprising a gas-liquid interface, a liquid-liquid interface, a lipid membrane, a polymer membrane, a nano-particle membrane, or a combination thereof. In some embodiments, the liquid-liquid interface may comprise a plurality of immiscible liquids. As used herein, the term "immiscible liquids" refers to a set of liquids that are incapable of mixing together (e.g. water and a hydrophobic liquid such as oil). In other embodiments, the liquid-liquid interface may comprise a thin physical barrier between the liquids, in which case the liquids may be immiscible or miscible. As used herein, the term "thin" refers to a membrane with a width of 2 to 100 nm. In some embodiments, the lipid membrane may comprise a lipid bilayer. In some embodiments, the polymer membrane may comprise a synthetically created membrane capable of enacting a driving force (e.g. pressure or concentration gradients) on particles on either side of the polymer membrane.

As used herein, "air" may refer to a gas or mixture of gasses, such as atmospheric air, oxygen, nitrogen, helium, neon, argon, an inert gas, or a reactive gas.

In a preferred embodiment, the present invention may feature a method for transfecting a cell. As a non-limiting example, the method may comprise providing a microfluidic platform (110) comprising a main microfluidic channel (120), and one or more cavity acoustic transducers (CATs) (130), wherein the one or more CATs (130) are dead-end channels coupled to the main microfluidic channel (120), wherein the microfluidic platform (110) is coupled to an external acoustic source (140); flowing a fluid (150) through the main microfluidic channel (120), said fluid (150) comprising a cell (160) and an exogenous material (170), wherein the fluid (150) intersects the CATs (130) to form one or more interfaces (180); and applying acoustic energy to the CATs (130) via the external acoustic source (140) to oscillate the interfaces (180), wherein oscillating the interfaces (180)

produces a plurality of microstreaming vortices (190) that trap cells (160) and exogenous material (170) therein, thereby applying shear to the cells (160), and allowing for delivery of the exogenous material (170) into the cell (160) through a plurality of uniformly sized pores generated by the shear. In some embodiments, the shear applied to the cells (160) may result in mechanical deformation of the cells (160). Hereinafter, the term "uniformly sized pores" means a plurality of pores of a plurality of cells wherein each pore is within a small standard deviation of each other. This may allow for the pores generated in the cells (160) to be large enough to accept exogenous material, but not so large as to damage the cell. In some embodiments, the dead-end of the channels may comprise a channel wall, a fluid front, a flexible membrane, or another interface. In some embodiments, the interfaces (180) may comprise a gas-liquid interface, a liquid-liquid interface, a lipid membrane, a polymer membrane, a nano-particle membrane, or a combination thereof. In some embodiments, the interfaces (180) may be 2 to 100 nm in width. In some embodiments, the interfaces (180) may be at least 2 nm in width. In some embodiments, the interfaces (180) may be at most 100 nm in width. In some embodiments, the interfaces (180) may be thin enough to avoid interrupting acoustic activity. In some embodiments, a configuration of the CATs (130) may be selected from a group comprising lateral to the main channel (120), above the main channel (120), below the main channel (120), and a combination thereof.

Referring now to FIG. 1, the present invention features a portable, automated, and high throughput device for cell transfection. In another preferred embodiment, the present invention may feature a system for intracellular delivery of an exogenous material. As a non-limiting example, the system may comprise a microfluidic platform (110) comprising a main microfluidic channel (120), and one or more cavity acoustic transducers (CATs) (130), wherein the one or more CATs (130) are dead-end channels coupled to the main microfluidic channel (120), wherein the microfluidic platform (110) is coupled to an external acoustic source (140); and a fluid (150) disposed through the main microfluidic channel (120), said fluid (150) comprising a cell (160) and an exogenous material (170), wherein the fluid (150) intersects the CATs (130) to form one or more interfaces (180). In some embodiments, the interfaces (180) may comprise a gas-liquid interface, a liquid-liquid interface, a lipid membrane, a polymer membrane, a nano-particle membrane, or a combination thereof. In some embodiments, the interfaces (180) may be 2 to 100 nm in width. In some embodiments, the interfaces (180) may be at least 2 nm in width. In some embodiments, the interfaces (180) may be at most 100 nm in width. In some embodiments, the interfaces (180) may be thin enough to avoid interrupting acoustic activity. In further embodiments, the CATs (130) may be configured to oscillate the interfaces (180) to produce a plurality of microstreaming vortices (190). Further, these vortices (190) may trap cells (160) and exogenous material (170) therein, thereby applying shear to the cells (160), and allowing for delivery of the exogenous material (170) into the cell (160) through a plurality of uniformly sized pores generated by the shear. In some embodiments, the shear applied to the cells (160) may result in mechanical deformation of the cells (160). In some embodiments, a configuration of the CATs (130) may be selected from a group comprising lateral to the main channel (120), above the main channel (120), below the main channel (120), and a combination thereof.

In some embodiments, a sequence of exogenous material types may be delivered to the plurality of cells (160) trapped within the microvortices (190). This may be achieved by directing the plurality of cells (160) through the main channel (120) such that they are trapped within the microvortices (190) generated by the CATs (130), directing a first cargo through the main channel (120) until every cell has received the first cargo, directing a second cargo through the main channel (120) until every cell has received the second cargo, and so on. In some embodiments, the plurality of microvortices (190) may allow for uniform mixing of cargos into cells.

In some embodiments, the CATs (130) may intersect the main channel (120) at an angle. As a non-limiting example, the angle may be between about 40-50 degrees. In other embodiments, the angle may be 1-10, 10-20, 20-30, 30-40, 50-60, 60-70, 70-80, or 80-90 degrees. In some embodiments, the method or system may have a transfection efficiency of at least about 20%. In some other embodiments, the method or system may have a transfection efficiency of at least about 5%, 10%, 15%, 20%, 25%, 30%, 35%, 40%, 45%, 50%, or greater than 50%.

In some embodiments, each CAT (130) may provide for the transfection of at least about 60,000 cells per minute. In some other embodiments, each CAT (130) may provide for the transfection of at least about 1,000, 2,000, 3,000, 4,000, 5,000, 6,000, 7,000, 8,000, 9,000, 10,000, 15,000, 20,000, 25,000, 30,000, 40,000, 50,000, 75,000, 100,000, 125,000, 150,000, 200,000 or more cells per minute. In some embodiments, the main microfluidic channel (120) may have a width with is about 0.1, 1, 2, 3, 4, 5, 6, 7, 8, 9, 10, 12, 14, 16, 18, 20, 25, 30, 35, 40, 50, 60, 70, 80, 90, 100, 120, 140, 160, 180, 200, 220, 240, 260, 280, 300, 350, 400, 450, 500, 600, 700, 800, 900, 1000, 1200, 1400, 1600, 1800, 2000, 2500, 3000, 4000, 5000, 6000, 7000, 8000, 9000, 10,000, or more micrometers. In some embodiments, the microstreaming vortices may induce a stress which is less than about 0.1, 1, 2, 3, 4, 5, 6, 7, 8, 9, 10, 12, 14, 16, 18, 20, 25, 30, 35, 40, 50, 60, 70, 80, 90, 100, 120, 140, 160, 180, 200, 220, 240, 260, 280, 300, 350, 400, 450, 500, 600, 700, 800, 900, 1000 or more Pa.

According to one embodiment, the microfluidic platform (110) may comprise a portable device, an automated device, a high throughput device, or a portable, automated, and high throughput device. According to another embodiment, the CAT (130) may induce pumping of the fluid (150), thereby eliminating the need for external pumping. In an alternative embodiment the microfluidic platform (110) may be coupled with an external pump. In still another embodiment, oscillation of the interfaces (180) may be controlled by a piezoelectric transducer (PZT) voltage. The transfection may be optimized by tuning the time the cells are trapped in the microstreaming vortices and the amplitude of the oscillation (by adjusting the PZT voltage).

In selected embodiments, deformation of the cells (160) may deform the cell membrane and cause it to be permeable to the exogenous material. In other selected embodiments, the cell (160) may be a human cell, a plant cell, an animal cell, an algae cell, a fungal cell, a bacterial cell, a prokaryotic cell, or a eukaryotic cell. In still other selected embodiments, the exogenous material (170) may comprise DNA, RNA, protein, a carbohydrate, a small molecule, or a combination thereof. In yet other selected embodiments, the method or system may be implemented in gene therapy, development of regenerative medicine, cancer treatments, or vaccines, in vitro fertilization, or an in vitro assay.

Figure 4:
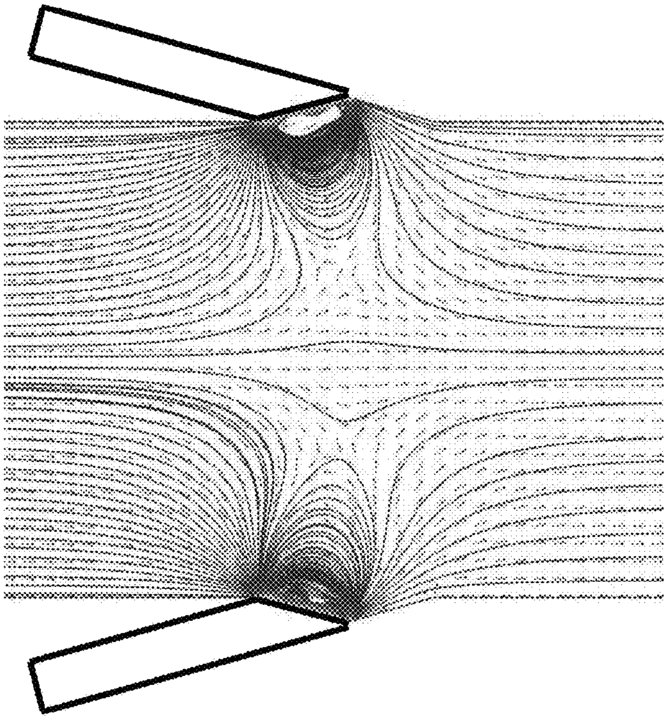
FIG. 4 shows a computer model simulation of the microstreaming vortices and the corresponding shear stresses.
Figure 5:
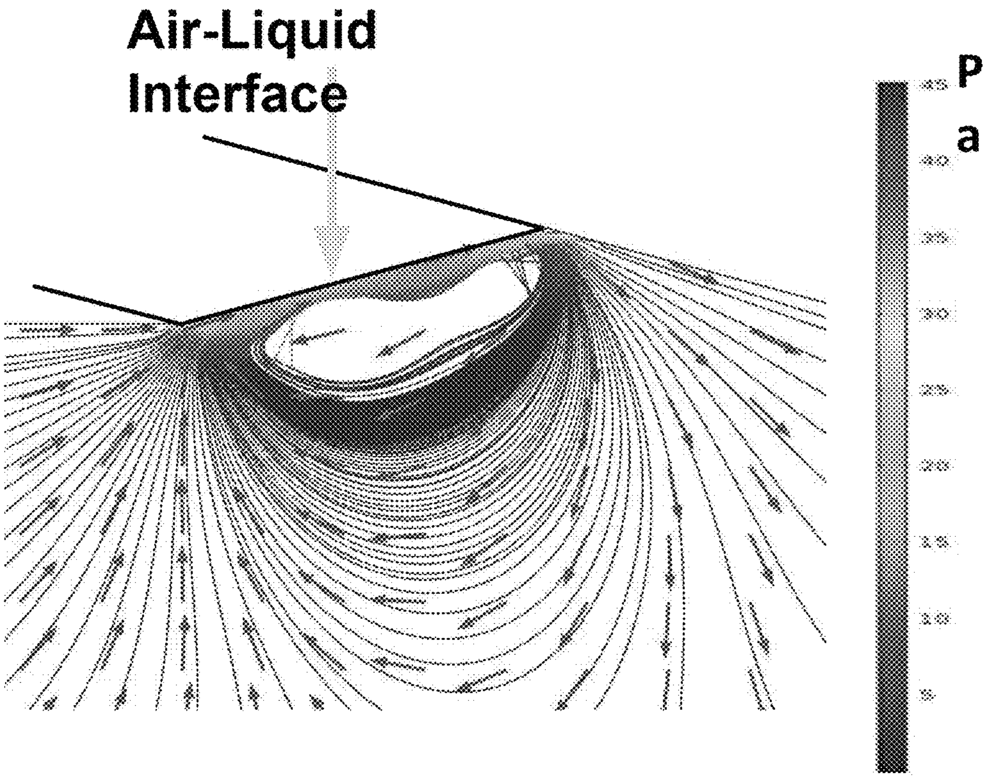
FIG. 5 shows a magnification of the computer model simulation of FIG. 4.
Figure 6:
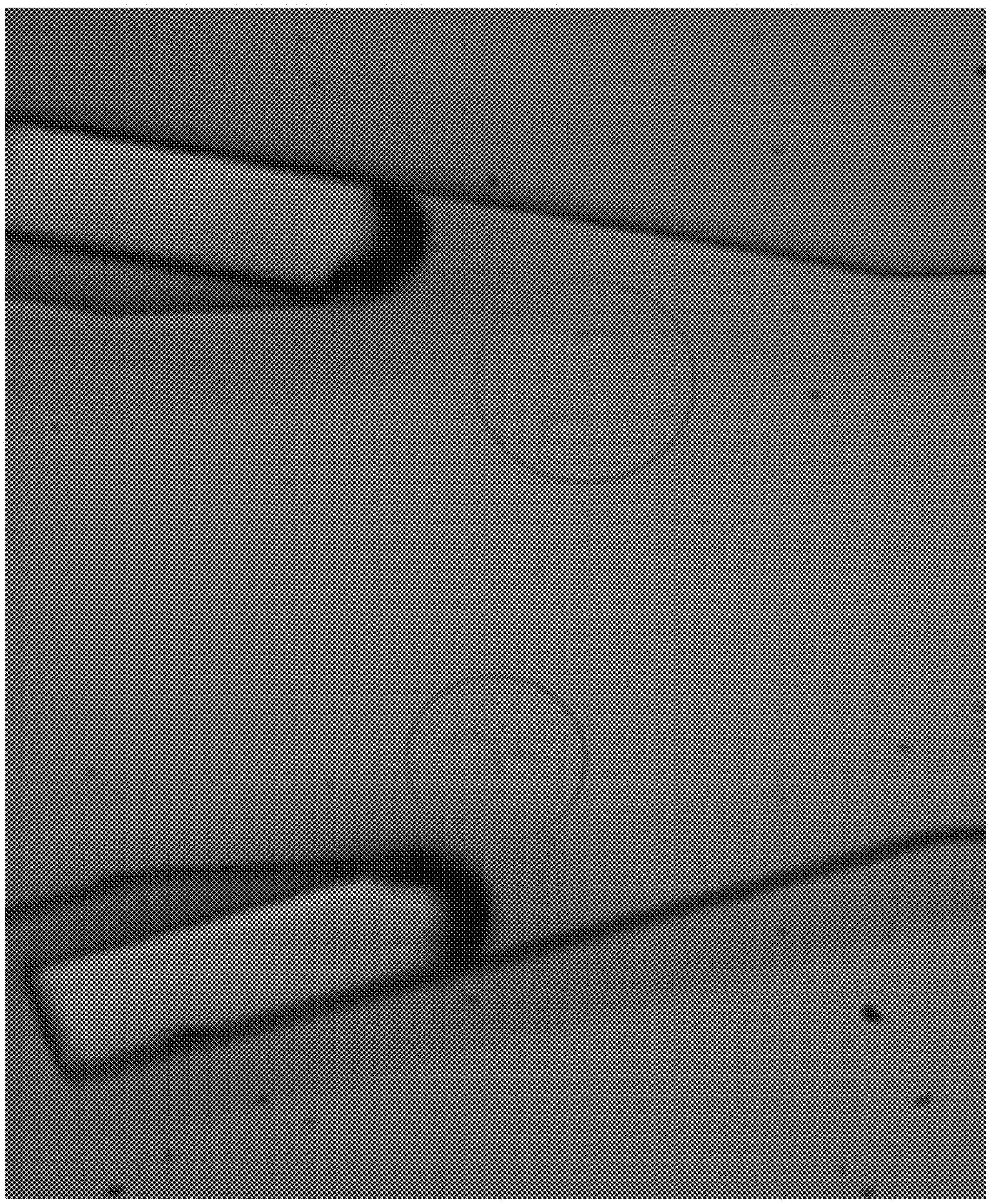
FIG. 6 shows a photograph showing experimental results which demonstrate shear-induced mechanical deformation of cells that are trapped inside the vortices.
Figure 7:
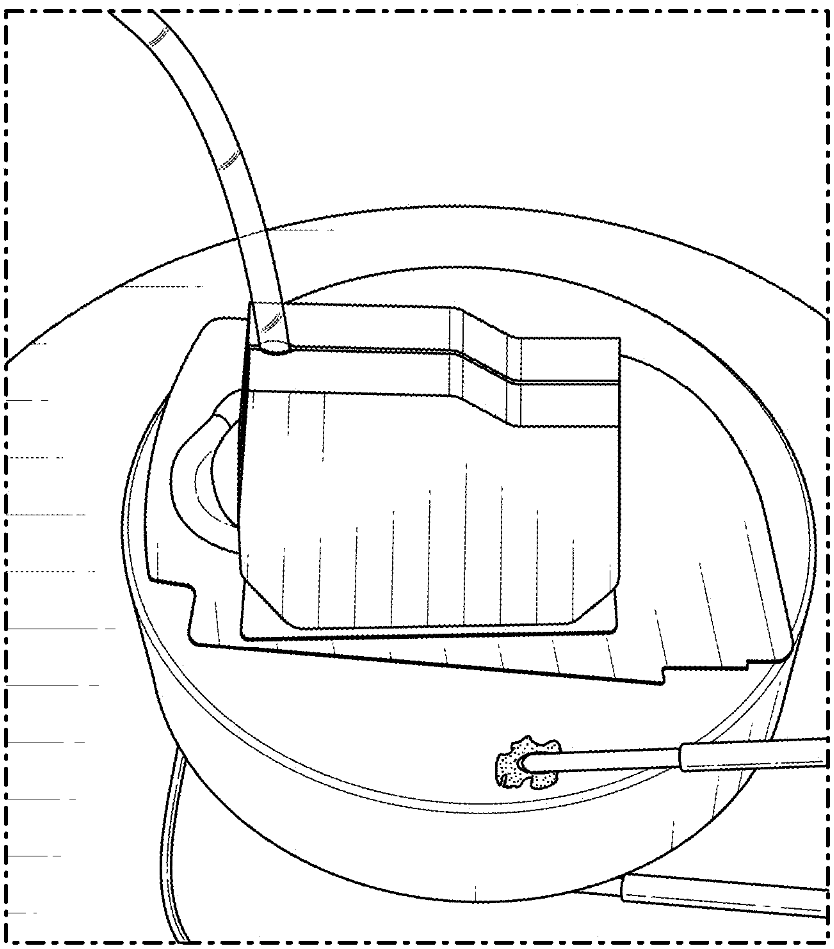
FIG. 7 shows a photograph of a CAT device of the present invention.
Figure 8:
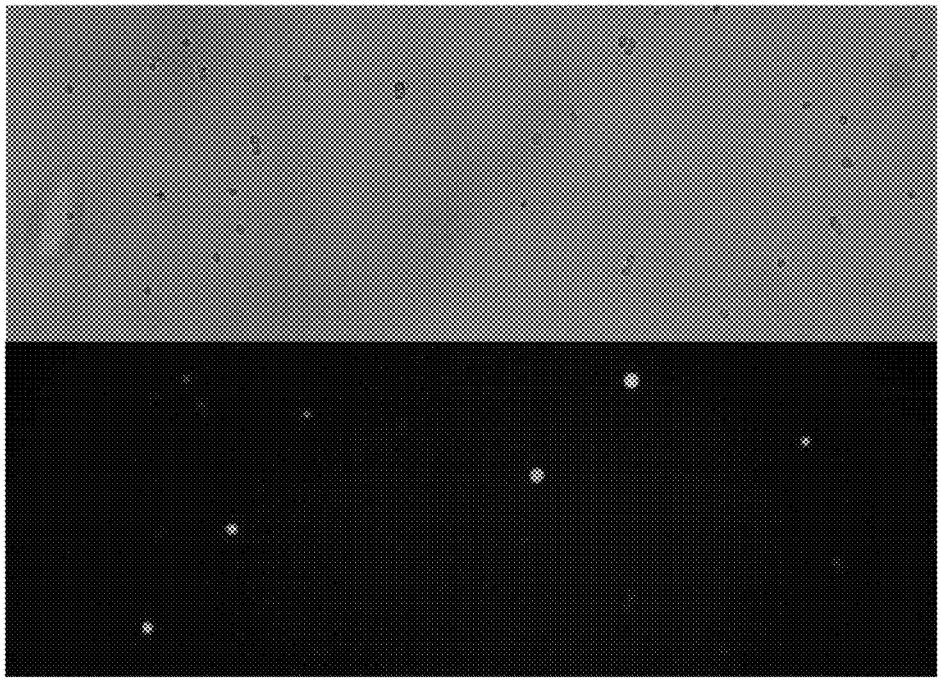
FIG. 8 shows bright-field and fluorescent images of the experimental group, in which the transfected cells can be identified by their emitted green fluorescence.
Figure 9:
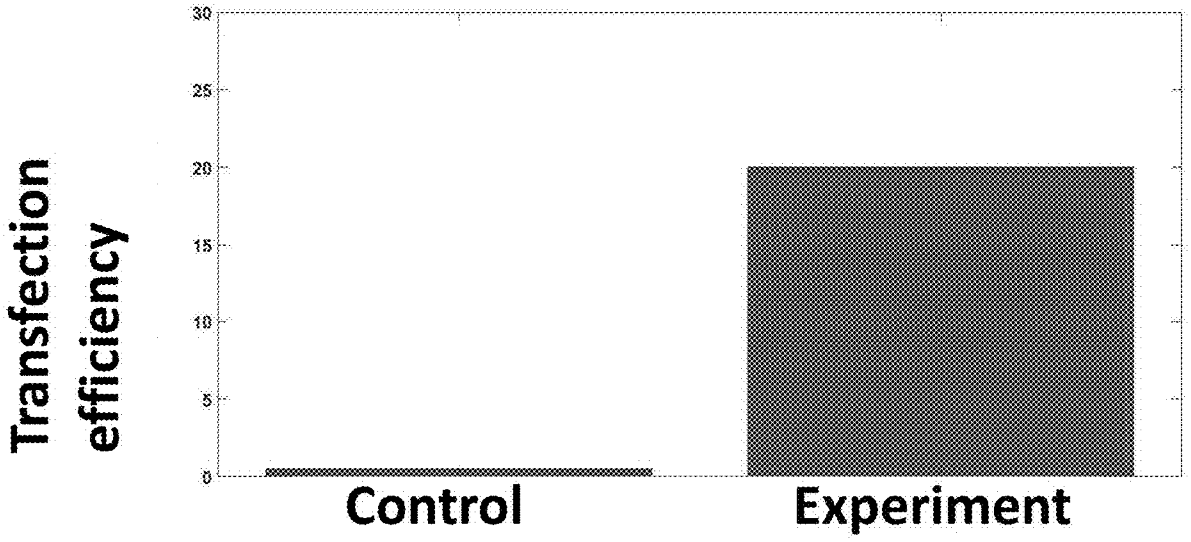
FIG. 9 shows a graph of cell transfection efficiency using 70 kDa dextran for both control (mixing dextran with cells and without CAT) and experimental (with CAT) groups.
Figure 10A:
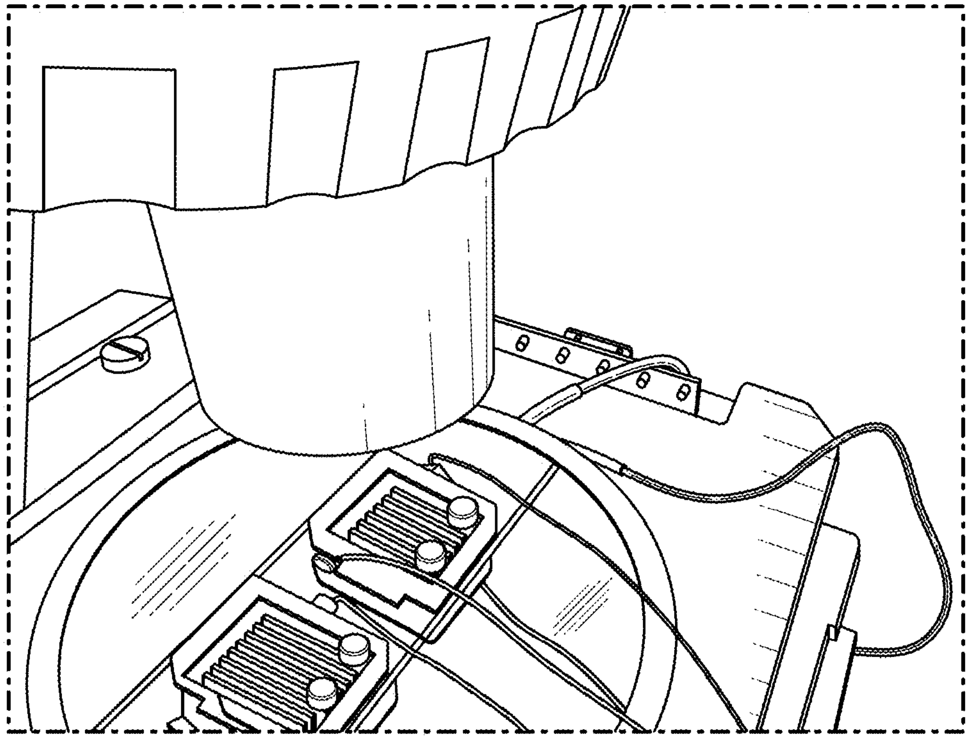
FIG. 10A shows a photograph of a CAT device setup with electrodes for electroporation.
Figure 10B:
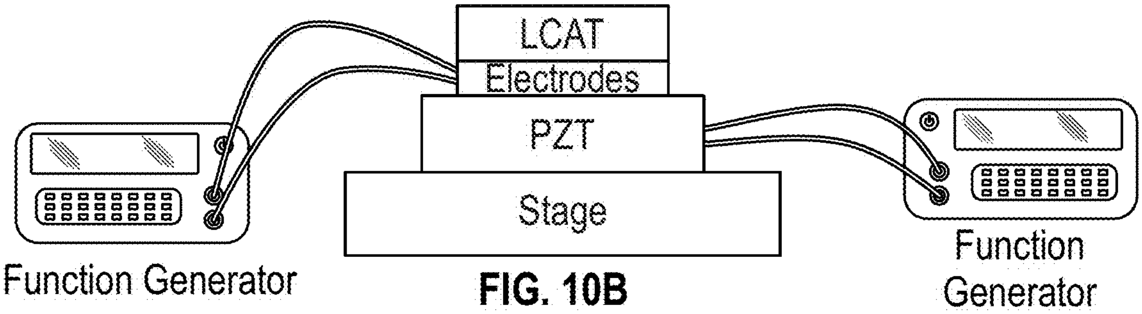
FIG. 10B shows a schematic illustration of the device setup in FIG. 10A.
Figure 10C:
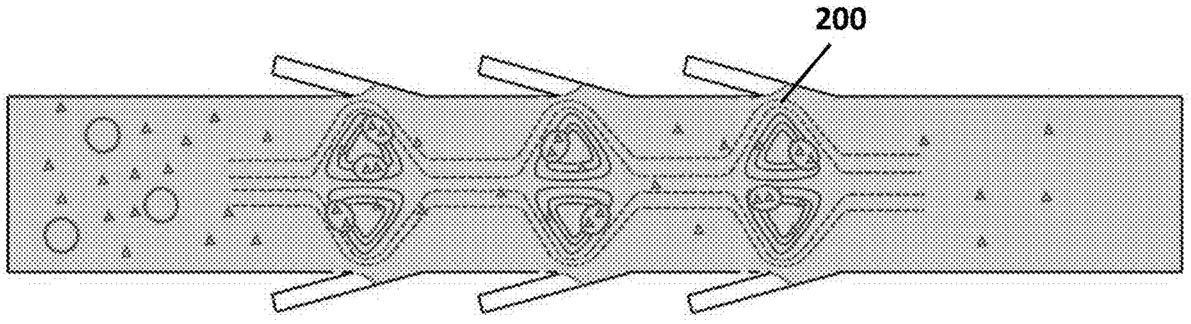
FIG. 10C shows a schematic of a CAT device integrated with arrays of interdigitated electrodes for intracellular delivery. Once the cells are selectively trapped inside the acoustic microstreaming vortices generated by CATs, they experience effective membrane disruption due the shear stress inside the vortices as well as the electric field. Such an effective membrane disruption coupled with highly efficient mixing facilitates delivery of exogenous materials into the cells.
Figure 10D:
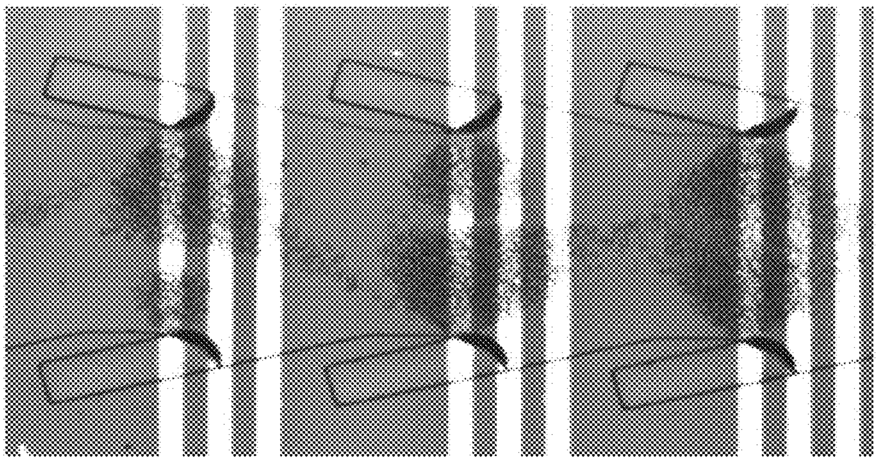
FIG. 10D shows a microscope image of Hela cells trapped inside vortices in the CAT device integrated with electrodes.

Referring now to FIG. 4, computational fluid dynamics (CFD) were used to model the microstreaming vortices near the interface. The results show that the cells experience significant shear stresses inside the vortices especially at the oscillating interface. Experimental results also confirm the presence of high shear stress in these regions as it induces mechanical deformation on cells that are trapped inside the vortices (FIG. 6). In contrast to the normal cells that are spherical, the deformed cells have elliptical shapes. Taking advantage of shear-induced mechanical deformation, the present invention utilized CAT for cell transfection. As can be seen from the results in FIG. 9, the device of the present invention could successfully achieve transfection efficiency of up to 20% for 70 kDa dextran. Without wishing to limit the invention to any particular theory or mechanism, it is believed that being trapped in vortices, the cells undergo mechanical deformation that creates transient membrane disruptions or holes in their membrane and facilitates delivery of exogenous materials into the cells.

Referring now to FIG. 1, the cells, passing the main channel, may be trapped in the microstreaming vortices that are generated by acoustically actuated interfaces in the devices. The trapped cells may experience shear stresses inside the vortices that facilitate their mechanical deformation.

Referring now to FIGS. 10A-D, the microfluidic device may additionally comprise an array of electrodes. The interdigitated electrodes may be fabricated on the main channel substrate and may be integrated with the microfluidic chip. In some embodiments, applying a voltage to the electrodes may be used to improve transient disruption of cell membranes via an electric field. This combination of mechanical deformation and electroporation may allow transfection of larger materials than mechanical deformation alone. Without wishing to limit the invention to any particular theory or mechanism, it is believed that the CATs allow for a gentle mechanical deformation which creates transient disruptions or pores in the cell membrane and electroporation may serve to expand these pores to promote transfection. Another advantage of this combination is that the cells are suspended in the fluid vortex and constantly 'tumbling' so that the electrical field applied is uniform across the whole surfaces of the cells (different angles are exposed throughout the tumbling in the vortices). The voltage and frequency of the electric signal applied to the electrodes may be tuned to modulate this electroporation effect. The PZT signal and the electroporation signal may be applied alternatively, simultaneously, or in overlapping but offset patterns. In some embodiments, the CATs (130) may be tuned to optimize exposure of the cells (160) to the voltage such that each cell (160) spends a near equal amount of time in the strongest portion of the voltage field. The array of electrodes (200) may be disposed above, below, or a combination thereof with respect to the microfluidic platform (110).

The present invention features a high-throughput method for transfecting a cell. In some embodiments, the method may comprise providing a microfluidic platform (110) comprising a main microfluidic channel (120), and one or more cavity acoustic transducers (CATs) (130). The one or more CATs (130) may be dead-end channels coupled to the main microfluidic channel (120). The microfluidic platform (110) may be coupled to an external acoustic source (140). The method may further comprise providing an array of electrodes (200), the electrodes interdigitated with the microfluidic platform (110). The method may further comprise flowing a fluid (150) through the main microfluidic channel (120), said fluid (150) comprising a cell (160) and an exogenous material (170). The fluid (150) may intersect the CATs (130) to form one or more interfaces (180). The method may further comprise applying acoustic energy to the CATs (130) via the external acoustic source (140) to oscillate the interfaces (180). Oscillating the interfaces (180) may produce a plurality of microstreaming vortices (190) that trap cells (160) and exogenous material (170) therein. The method may further comprise applying a voltage to the electrodes (200) so as to achieve electroporation of the cells (160) allowing for delivery of the exogenous material (170) into the cell (160) through a plurality of uniformly sized pores generated by the electroporation.

In some embodiments, the CATs (130) may be tuned to optimize exposure of the cells (160) to the voltage. In some embodiments, the array of electrodes (200) may be disposed above, below, or a combination thereof with respect to the microfluidic platform (110). In some embodiments, the CATs (130) may intersect the main channel (120) at an angle. The microfluidic platform (110) may comprise a portable, automated, and high throughput device. The electrodes may be capable of at least a first mode and a second mode. The first mode may achieve generation of pores in the cells (160), and the second mode may achieve widening of said pores generated in the first mode. In some embodiments, the oscillation may be controlled by a piezoelectric transducer (PZT) voltage. The CAT (130) may induce pumping of the fluid (150), thereby eliminating the need for external pumping. This method may have a transfection efficiency of at least about 20%. The cell (160) may be a human cell, a plant cell, an animal cell, an algae cell, a fungal cell, a bacterial cell, a prokaryotic cell, or a eukaryotic cell. The exogenous material (170) may comprise DNA, RNA, protein, a carbohydrate, a small molecule, or a combination thereof. In some embodiments, a configuration of the CATs (130) may be selected from a group comprising lateral to the main channel (120), above the main channel (120), below the main channel (120), and a combination thereof. The interfaces (180) may comprise a gas-liquid interface, a liquid-liquid interface, a lipid membrane, a polymer membrane, a nano-particle membrane, or a combination thereof. The interfaces (180) may be 2 to 100 nm in width.

In some embodiments, the array of electrodes (200) may be positioned perpendicular to the main channel (120). In other embodiments, each electrode of the array of electrodes (200) may be positioned at an angle of 0° to 90° with respect to the main channel (120). The electrodes (200) may also be in a zig-zag or serpentine configuration in order to increase the field density and uniformity of the voltage applied to the cells (160). In the main application, the present invention has implemented 3 electrodes beneath each microstreaming vortex. However, this number can range from 2 to a case where it covers the whole bottom of the main channel (e.g., FIG. 16C).

Figure 16A:
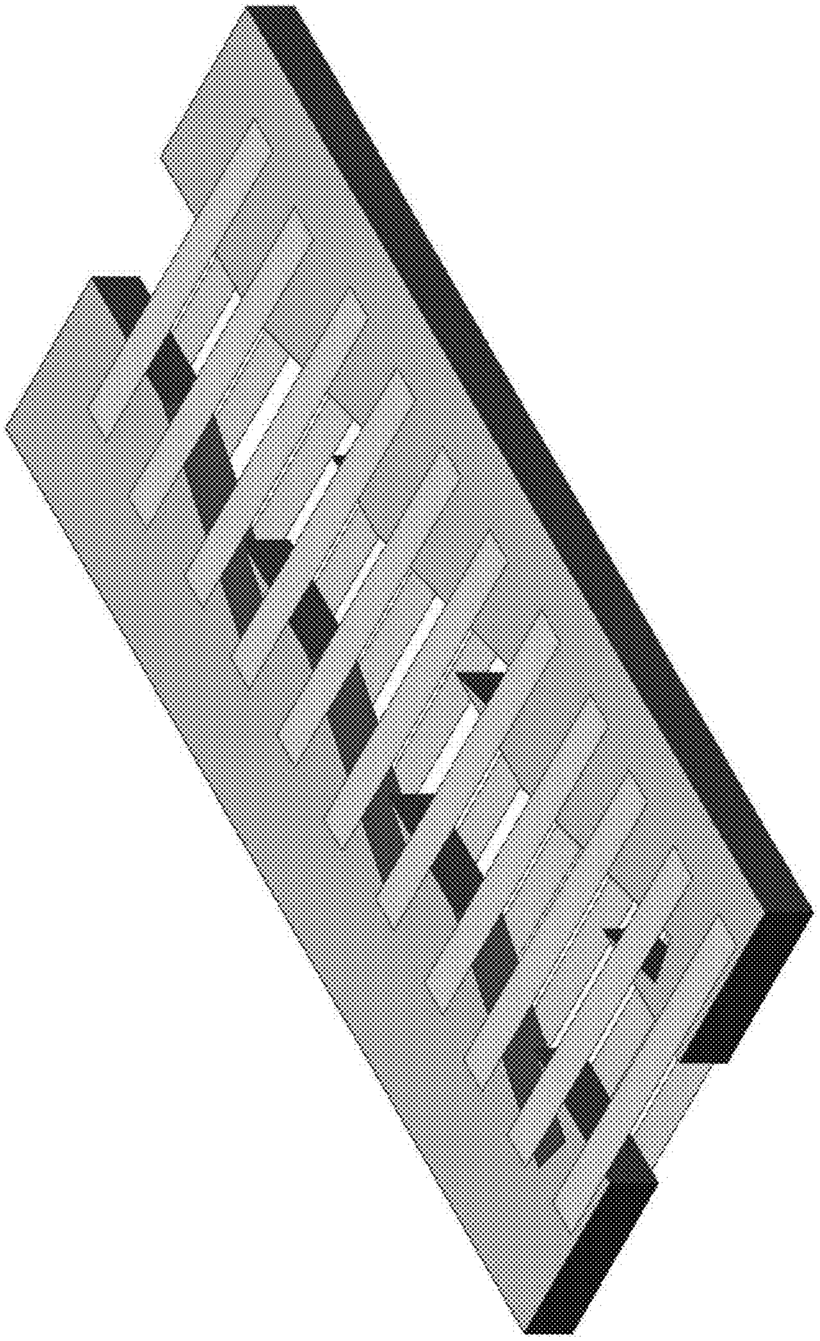
FIG. 16A shows an embodiment of the device of the present invention where one set of electrodes are positioned on top and the other set on the bottom of the channel and have a 90° angle with the main CAT channel.
Figure 16B:
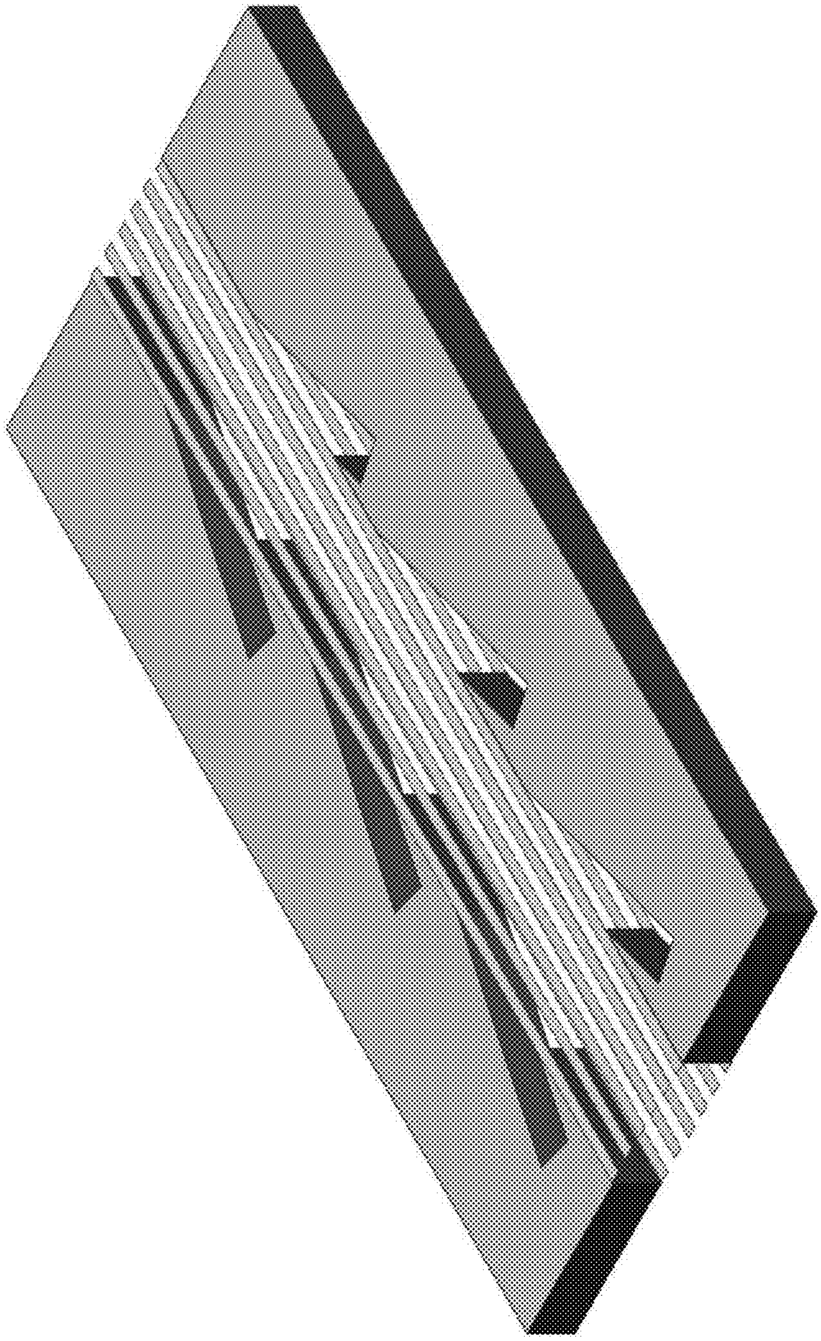
FIG. 16B shows an embodiment of the device of the present invention where one set of electrodes are positioned on top and the other set on the bottom of the channel and have a 0° angle with the main CAT channel.
Figure 16C:
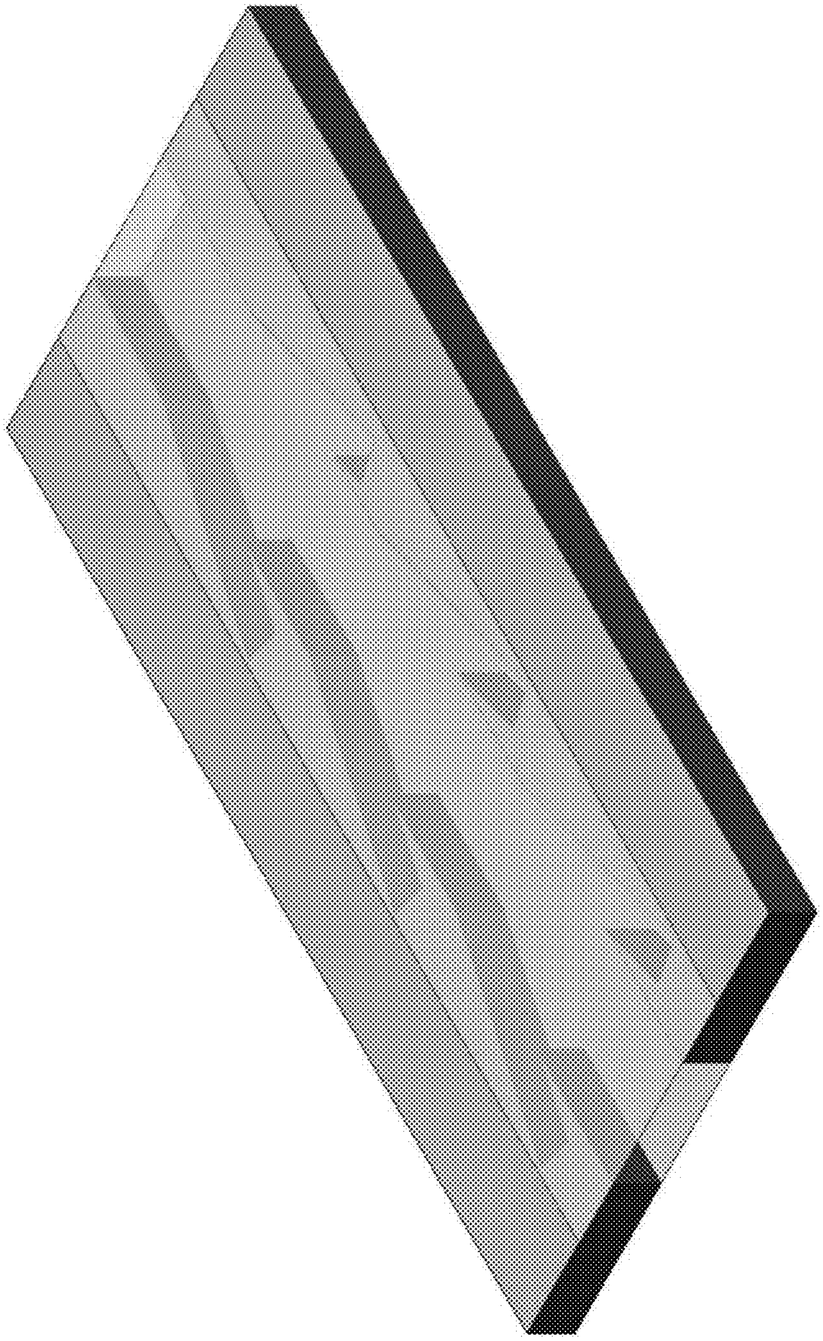
FIG. 16C shows an embodiment of the device of the present invention where electrodes cover the whole top and bottom of the channel.

There is an additional set of configurations that cannot be categorized in IDA electrodes or IDEs. This is for the case where one set of electrodes are on the bottom of the channel and the other set on top of the channel. For convenience, hereafter these electrodes are called bottom and top electrodes. FIGS. 16A-16C show the proposed configurations. FIGS. 16A and 16B show configurations where electrodes have a 90° and 0° angle with respect to the main CAT channel, respectively. However, this angle can be any value between 0° and 90°. They can also be in a zig-zag or serpentine configuration in order to increase the field density and uniformity. In addition, as for top and bottom electrodes, any combination between the three proposed configurations is possible (e.g., top electrodes from FIG. 16A with bottom electrodes from FIG. S4C).

In some embodiments, the fluid flow in the microfluidic device is pressure-driven. For example, the microfluidic device may further include a microfluidic pump operatively connected to at least one of the channels. In some embodiments, the microfluidic pump may be a pneumatic pump.

In other embodiments, the transfection reagents may comprise one or more species of cationic lipids. In yet other embodiments, the transfection reagents may comprise one or more species of cationic lipids and a helper lipid.

In some embodiments, the cells may be eukaryotic cells, prokaryotic cells, or a combination thereof. In one embodiment, the eukaryotic cells may be animal cells, plant cells, algae cells, fungal cells, or a combination thereof. In another embodiment, the prokaryotic cells are bacterial cells. In other embodiments, the cells may be protoplasts, pollen grains, microspores, tetrads, or a combination thereof.

Transfection Molecules

Nucleic acid, e.g., DNA or RNA, is the most commonly transfected molecule. However, the present invention is not limited to transfection of DNA or RNA. In some embodiments, the molecule that is transfected is DNA, RNA, a protein, a carbohydrate, a small molecule (e.g., a drug), beads, barcoded beads, the like, or a combination thereof. In some other embodiments, the transfection molecule may be a targeting complex comprising a DNA-targeting RNA bound to Cas9 polypeptide, also referred to as a Cas9 nuclease, which forms a DNA-targeting RNA and Cas9 complex. The Cas9 may be naturally-occurring, a derivative, or modified Cas9. In other embodiments, the transfection molecule may be a targeting complex comprising a DNA-targeting RNA bound to a site-active polypeptide other than Cas9. In other embodiments, the transfection molecule may be a targeting complex that can be used in CRISPR-Cas gene editing. For example, the transfection molecule is the DNA-targeting RNA and Cas9 complex for CRISPR-Cas9. In some other embodiments, the transfection molecule for CRISPR-CAS9 may be a DNA vector encoding sgRNA, a DNA vector encoding CAS9 nuclease gene, DNA vector encoding both sgRNA and CAS9 nuclease gene, an sgRNA or other RNA molecules, a CAS9 nuclease or other protein molecules, an sgRNA-CAS9 complexes, or other DNA or RNA and protein complex.

Transfected Cells

Any particular cell type from any organism may be used in the methods and systems of the present invention, namely any cell suitable for transfection. In some embodiments, the cells may be wild type cells or genetically modified cells. In other embodiments, the cells may be cells harboring one or more mutations, healthy cells, diseased cells or unhealthy cells, etc. For example, in some embodiments, the cells may be prokaryotic cells (e.g., bacteria, archaebacteria, etc.). In other embodiments, the cells may be eukaryotic cells such as single-celled eukaryotes, fungal cells (e.g. yeast, mold, etc.), animal cells, mammalian cells (e.g. cells from a human, non-human primate, rodent, rabbit, sheep, dog, cat, etc), and non-mammalian cells (e.g. cells from insects, reptiles, amphibians, birds, etc.).

In some embodiments, the cells used in the present invention may be other eukaryotic cells such as plant cells or algal cells. Non-limiting and non-exhaustive examples of plant cells include cells from corn, soybean, wheat, cotton, grass, flowering plants, fruit-bearing plants, trees, tuberous plants, potatoes, root plants, carrots, peanut, nuts, beans, legumes, and squashes. It is to be understood that the term "plant cell" encompasses all types and stages of plant cells and is not limited to the aforementioned examples. Non-limiting and non-exhaustive examples of algal cells include cells from *Chlorella* sp., *Nannochloropsis* sp, and *Botryococcus* sp. It is to be understood that the term "algal cell" encompasses all types of algal cells and is not limited to the aforementioned examples. One of the distinguishing characteristics that plant and algal cells have over animal cells is a cell wall that surrounds a cell membrane to provide rigidity, strength, and structure to the cell. The cell wall may be comprised of polysaccharides including cellulose, hemicellulose, and pectin. Similar to plant and algal cells, the fungal cells also have a cell wall, which may be comprised of polysaccharides including glucans, mannans, and chitin. In some embodiments, the microfluidic systems and methods described herein may allow for transfection through the cell wall as well as the cell membrane.

In other embodiments, the cells used in the present invention may be protoplasts, which are intact plant, bacterial or fungal cells that had its cell wall completely or partially removed using either mechanical or enzymatic means.

In yet other embodiments, the cells used in the present invention may be a tetrad. The term "tetrad" is used to herein to refer to a single structure comprised of four individual physically attached components. A "microspore" is an individual haploid structure produced from diploid sporogenous cells (e.g., microsporocyte, pollen mother cell, or meiocyte) following meiosis. A microspore tetrad refers to four individual physically attached microspores. A "pollen grain" is a mature gametophyte containing vegetative (non-reproductive) cells and a generative (reproductive) cell. A pollen tetrad refers to four individual physically attached pollen grains.

As used herein, the microfluidic devices employ fluid volumes on the scale of microliters ($10^{-6}$) to picoliters ($10^{-12}$) that are contained within sub-millimeter scale channels. The structural or functional features may be dimensioned on the order of mm-scale or less. For example, a diameter of a channel or dimension of a chamber may range from <0.1 μm to greater than 1000 μm. Alternatively or in addition, a length of a channel may range from 0.1 μm to greater than cm-scale.

As used herein, the term "about" refers to plus or minus 10% of the referenced number.

EXAMPLE

The following is a non-limiting example of the present invention. It is to be understood that said example is not intended to limit the present invention in any way. Equivalents or substitutes are within the scope of the present invention.

Example 1: Experimental Protocol

Dextran was prepared at the concentration of 20 mg/mL in PBS buffer and mixed with the cell sample at 1:1 ratio. The mixed sample was then introduced at the device inlet. The PZT frequency and voltage amplitude were set to 50.2 kHz and 4 Vpp, respectively. This resulted in acoustic microstreaming vortices in the CAT device (with 500 microns width and 100 microns height) that were able to trap cells larger than 10 microns in size. The device was then run for 5 minutes. Throughout 5 minutes operation of the CAT device, an AC electric field of 10 Vpp with frequency of 10 KHz was applied for three times (each cycle 1 s). The cells were then collected from the outlet and incubated for 1 hour at 37 degrees Celsius. After incubation, the cells were washed three times with PBS and flow cytometry were performed.

Example 2: System Description

Summary

In one embodiment, the present invention features a multimodal, portable, and integrated platform based on cavity induced acoustic microstreaming and on-chip electroporation for size-selective and efficient intracellular delivery of exogenous materials.

Introduction

Intracellular delivery of exogenous materials is an important, yet challenging, step in basic biological research as well as in therapeutic applications. Microfluidic methods of the present invention allow for high throughput and efficient intracellular delivery of biomolecules. The platform, within a single step, facilitates intracellular delivery by: (i) shear-induced mechanical deformation, (ii) on-chip electroporation for transiently disrupting the cell membrane, and (iii) efficient mixing of the exogenous materials to enter into cells. Compared to existing methods, the present system not only can deliver a wide range of molecular sizes at high efficiency, but it also offers unique sample processing advantages. For example, the unique design of Cavity Acoustic Transducers (CATs) generates a bulk flow that eliminates the need of external pumping. In addition, the presented platform is capable of size-based selective transfection which is a unique feature for applications where transfection of specific cellular population is targeted. Furthermore, since cells are trapped and suspended in microstreaming vortices, the microfluidic channels are wider, making them higher throughput and less clog-prone than other microfluidic transfection devices that typically flow cells one-by-one and have channel dimensions at the scale of single cells.

Concept:

CATs are arrays of acoustically actuated interfaces generated using dead-end channels as shown in FIGS. 10A-D. The oscillating interfaces in CATs result in microstreaming vortices capable of size selective trapping of cells. The trapped cells in these vortices experience shear stresses causing mechanical deformation, which can be controlled by varying interface oscillation amplitude using piezoelectric transducer (PZT) voltage. The induced mechanical deformation creates transient disruptions or pores in the cell membrane and facilitates delivery of exogenous materials. In addition, to efficiently deliver larger sized molecules (>10-kDa) into the cells, the arrays of interdigitated electrodes are integrated to the chip in order to improve the transient disruption of cell membranes via electric field.

Results & Discussion

Figure 11A:
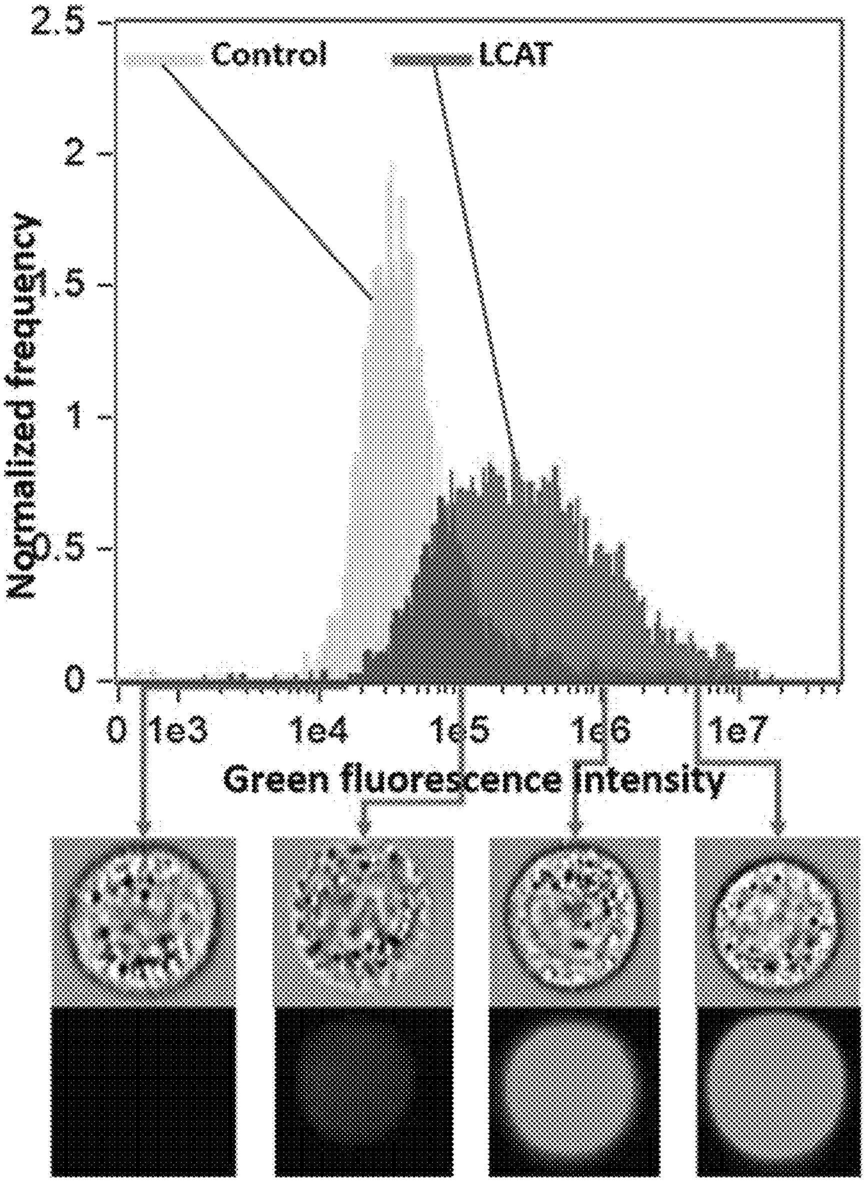
FIGS. 11A and 11B show an evaluation of delivery efficiency of 3-KDa dextran into HeLa cells.
Figure 11B:
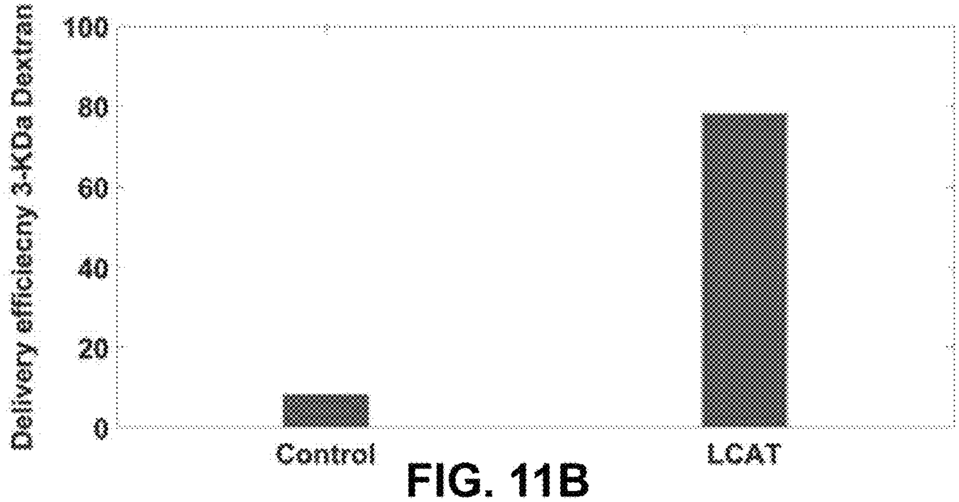
Figure 12A:
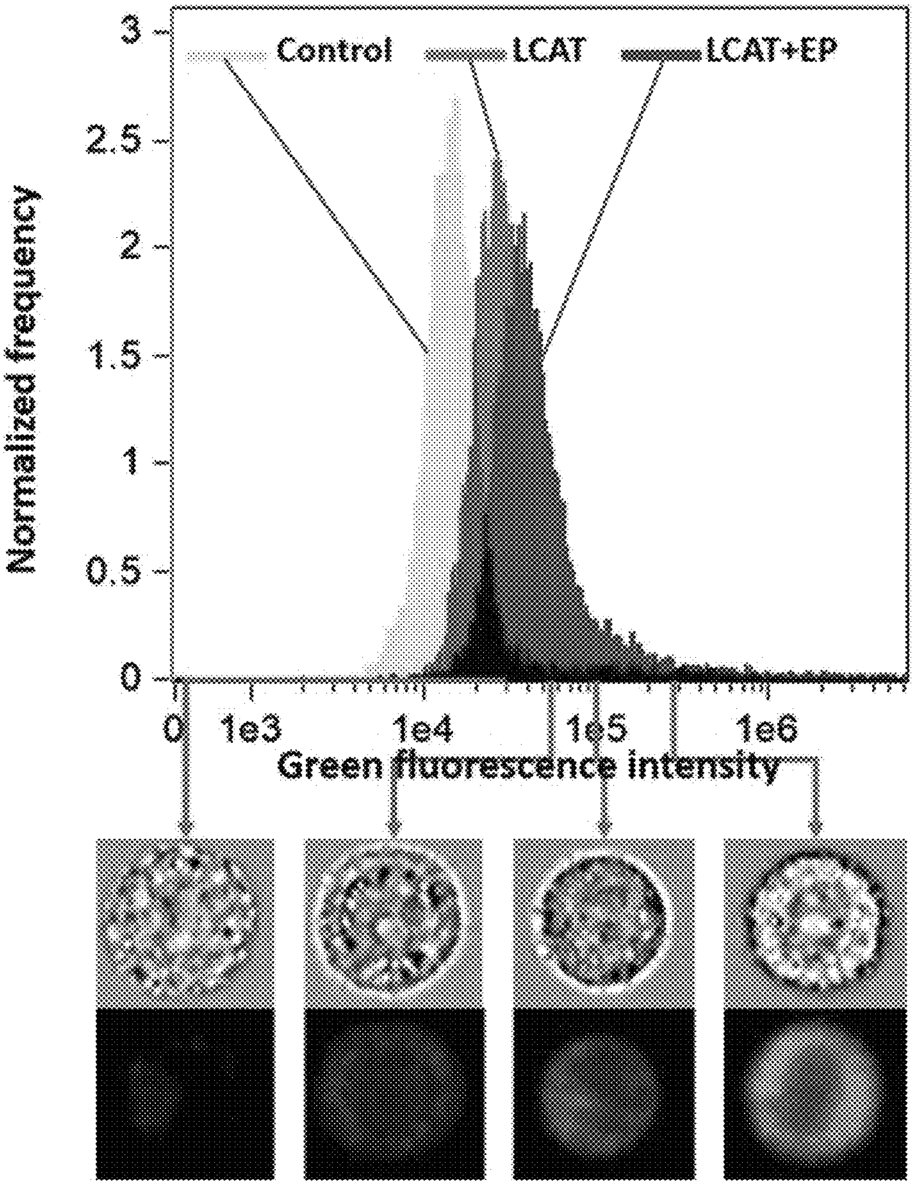
FIGS. 12A and 12B show an evaluation of delivery efficiency of 70-KDa dextran into HeLa cells.
Figure 12B:
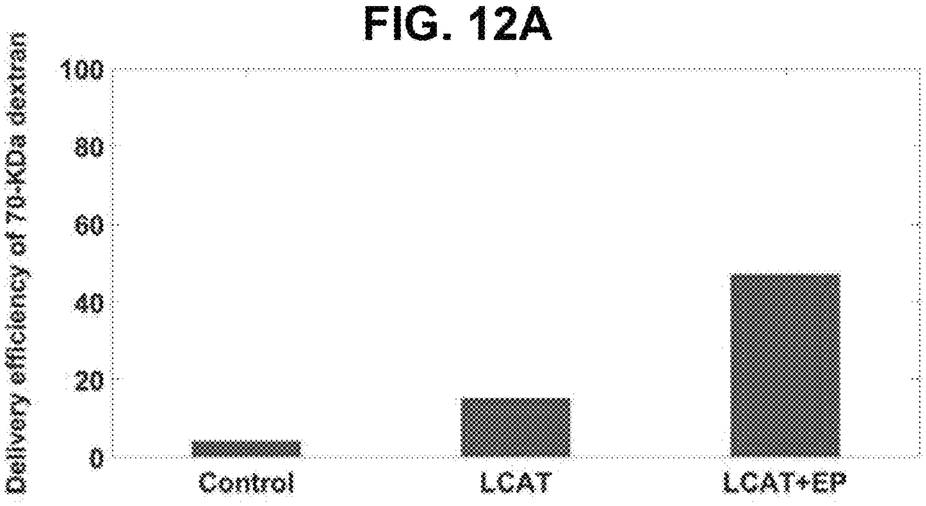
Figure 13A:
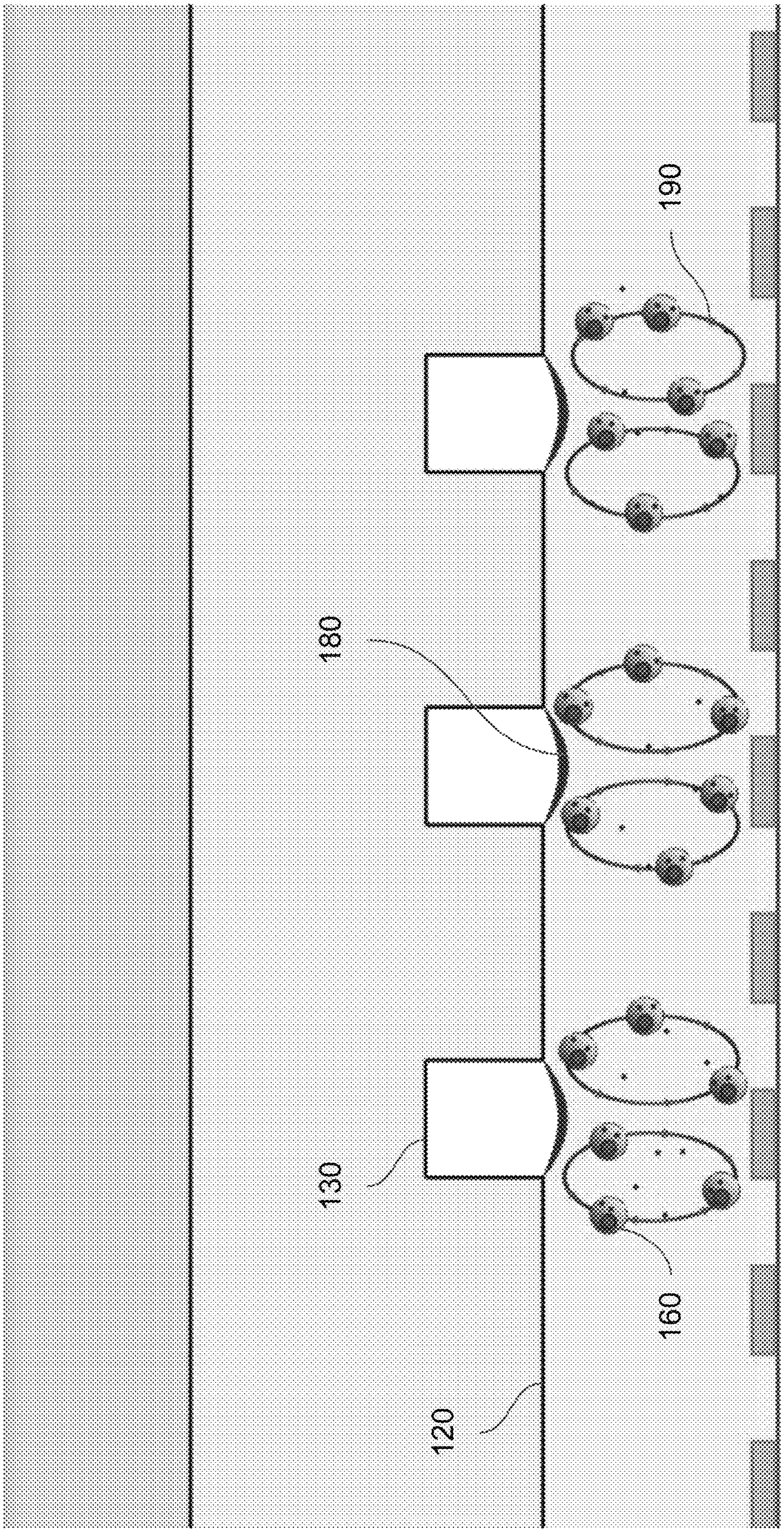
FIGS. 13A and 13B show various vertical configurations of the CATs with respect to the microfluidic platform of the present invention. The PZT may be disposed above or below the microfluidic platform, respectively.
Figure 13B:
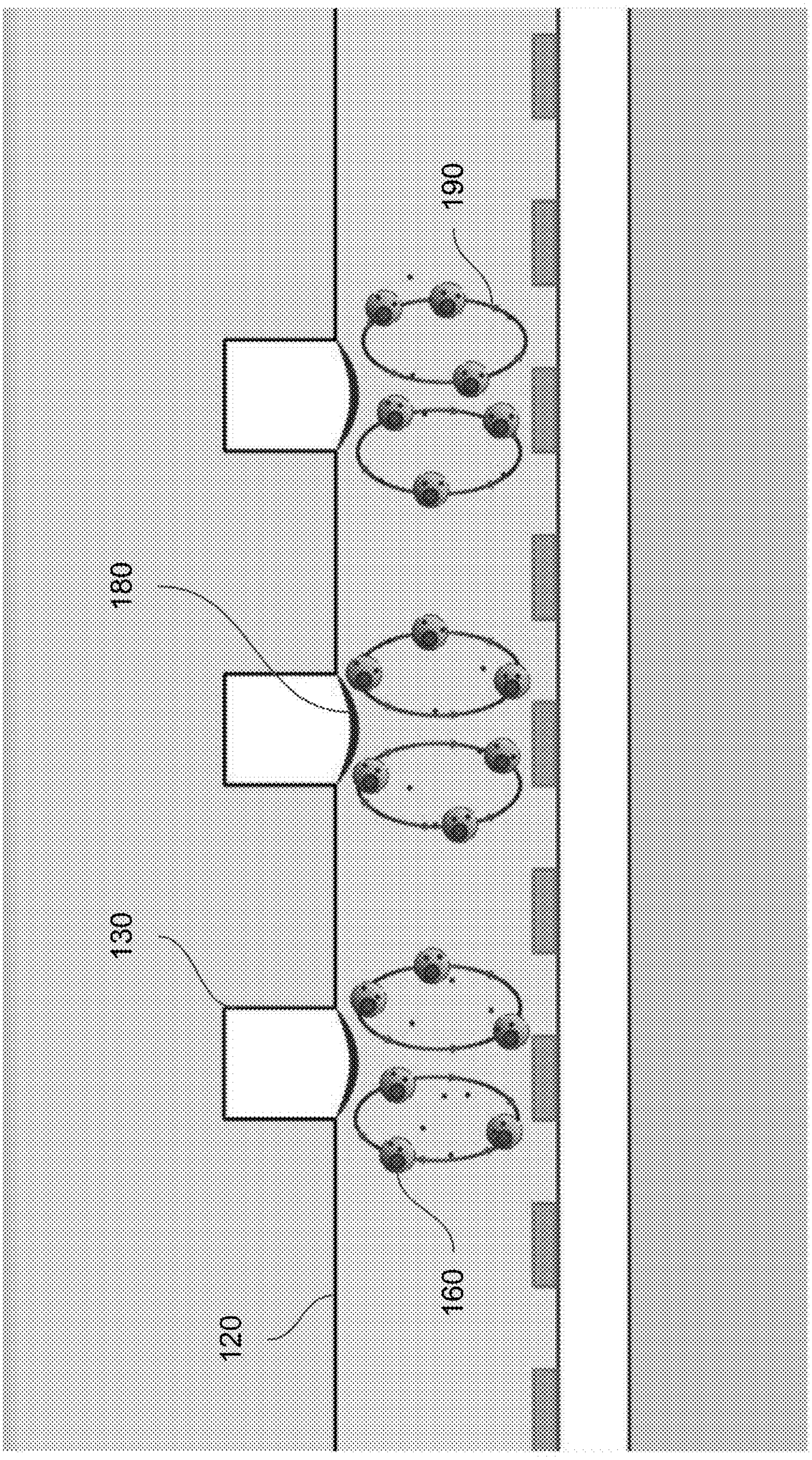
Figure 13C:
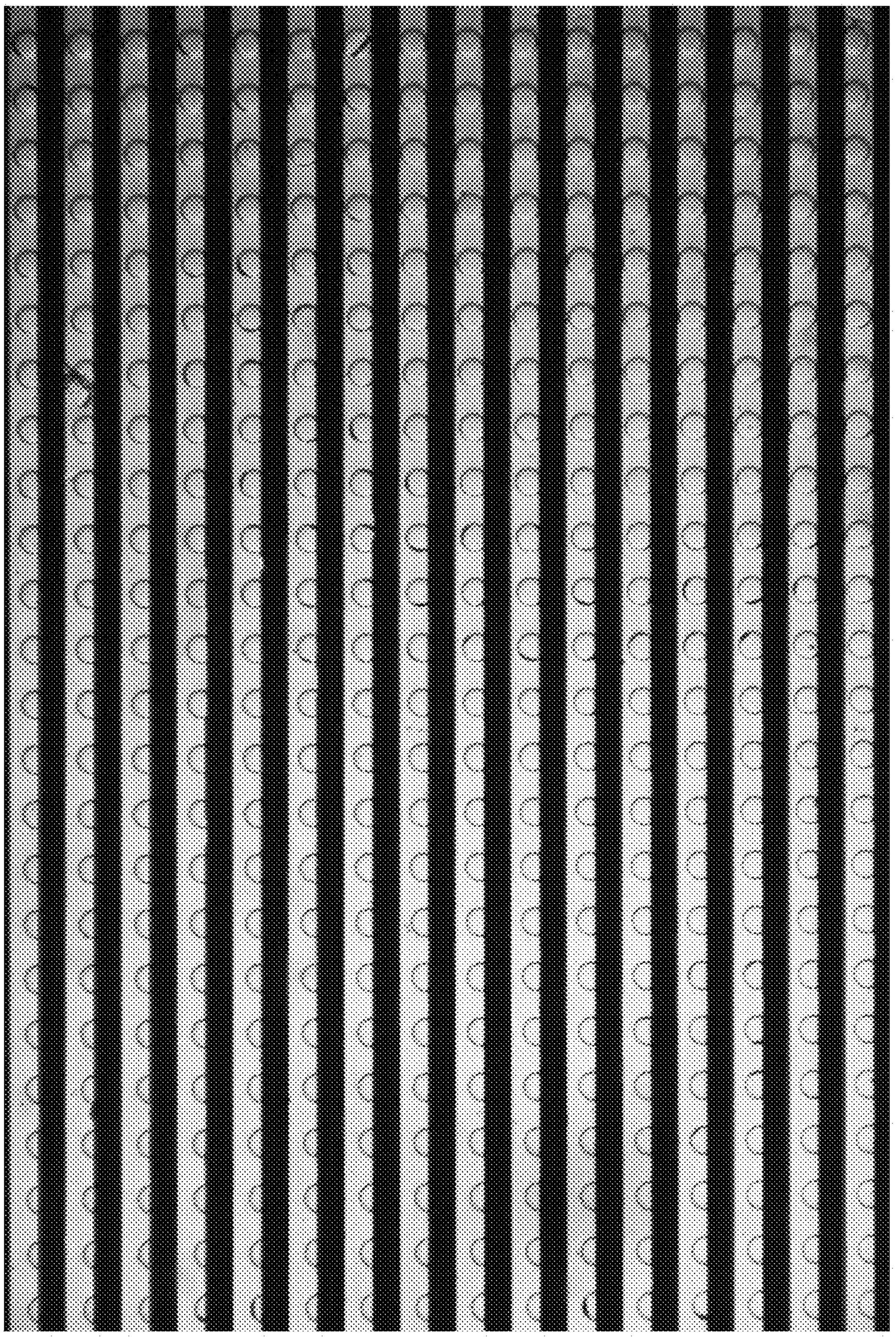
FIG. 13C shows a top view of vertical cavity acoustic transducers (VCATs) with arrays of interdigitated electrodes on the bottom.
Figure 14A:
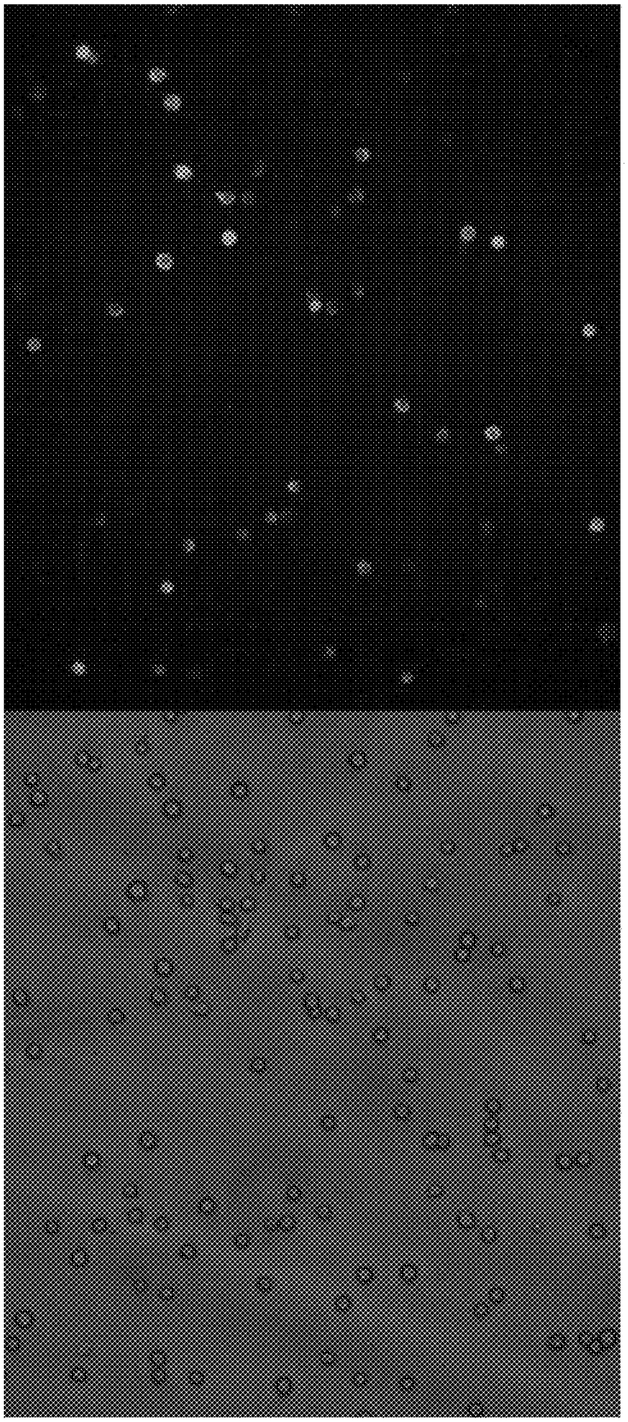
FIG. 14A shows a bright-field and fluorescent images of the experimental group, in which the transfected cells by VCAT integrated with interdigitated electrodes can be identified by their emitted green fluorescence.
Figure 14B:
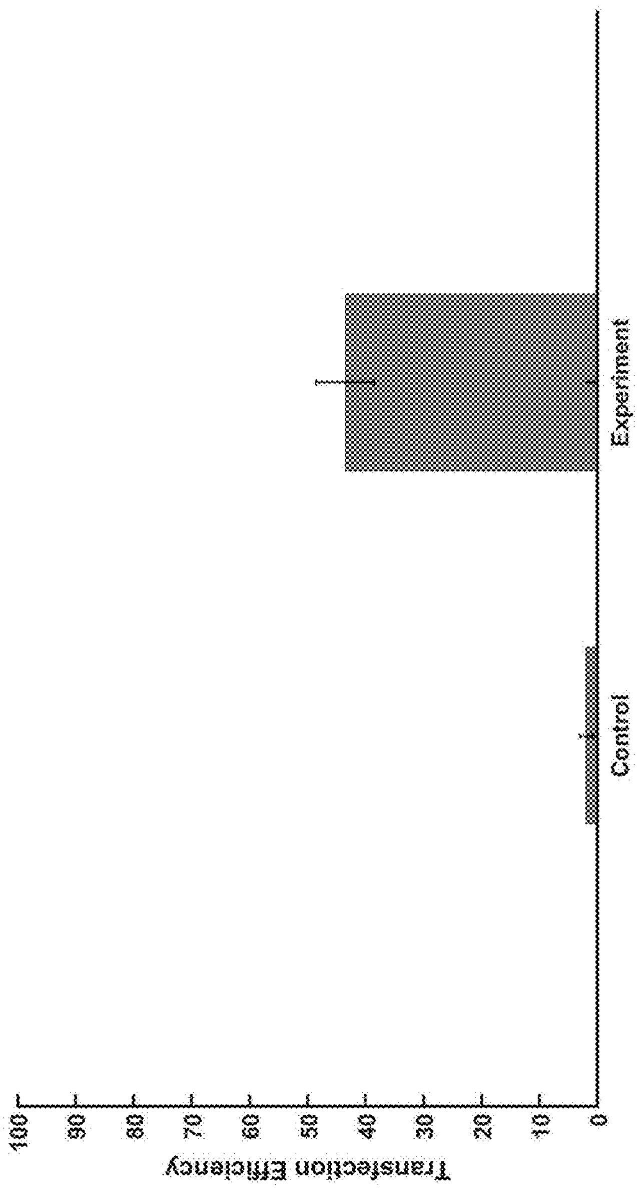
FIG. 14B shows the transfection efficiency of 2-MDa Dextran molecule into Jurkat cells. For this experiment, an AC electric field of 25 Vpp with frequency of 10 KHz and duration of 50 ms was applied to the interdigitated electrodes. The PZT frequency and voltage amplitude were set to 50.2 kHz and 10 Vpp, respectively.
Figure 15:
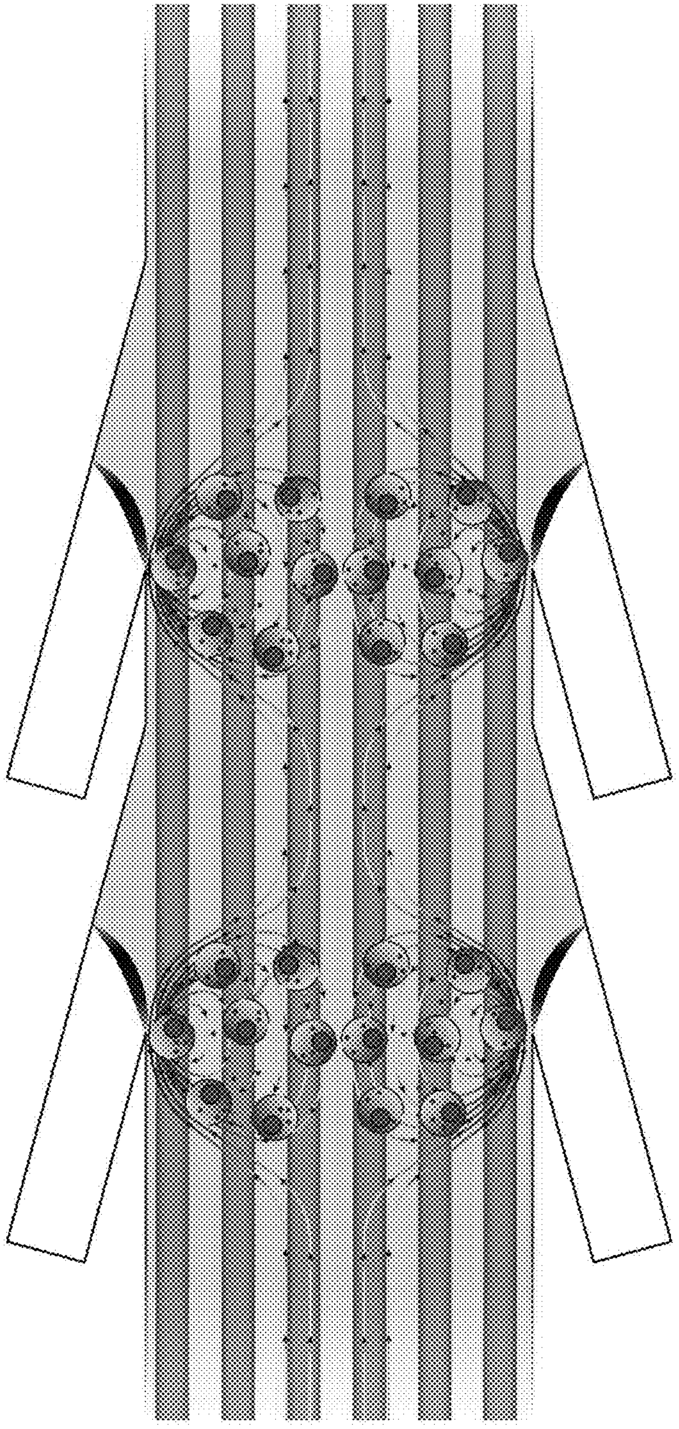
FIG. 15 shows an embodiment of the device of the present invention where the array of interdigitated electrodes are parallel to the main fluidic channel.

To evaluate the device performance, 3 and 70-kDa dextran were delivered into Hela cells with the average diameter of 15 microns. The two selected dextran sizes were chosen to represent majority of siRNA molecules and proteins, respectively. As shown in FIGS. 11A-B, high delivery efficiency of 80% is achieved for 3-kDa dextran using CAT device alone. For these small sized molecules, shear-induced mechanical deformation in acoustic microstreaming vortices creates enough transient holes in cell membranes for efficient delivery. As for delivery of 70-kDa, CAT device alone results in delivery efficiency of 15%; however, by electroporation integrated CAT device, a higher delivery efficiency of 45% (FIGS. 12A-B) was achieved while maintaining cell viability above 90%.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A high-throughput transfection method, comprising:

a. providing a microfluidic platform (110) comprising a main microfluidic channel (120), and one or more cavity acoustic transducers (CATs) (130), wherein the one or more CATs (130) are dead-end channels coupled to the main microfluidic channel (120), wherein the microfluidic platform (110) is coupled to an external acoustic source (140);

b. flowing a fluid (150) through the main microfluidic channel (120), wherein the fluid (150) intersects the CATs (130) to form one or more interfaces (180); and c. applying acoustic energy to the CATs (130) via the external acoustic source (140) to oscillate the interfaces (180), wherein oscillating the interfaces (180) produces a plurality of microstreaming vortices (190) that causes shear-induced mechanical deformation.

2. The method of claim 1, additionally comprising:

a. providing an array of electrodes (200), the electrodes interdigitated with the microfluidic platform (110); and b. applying a voltage to the electrodes (200) so as to achieve electroporation.

3. The method of claim 1, wherein the oscillation is controlled by a piezoelectric transducer (PZT) voltage.

4. The method of claim 1, wherein the CAT (130) induces pumping of the fluid (150), thereby eliminating a need for external pumping.

5. The method of claim 1, wherein the fluid (150) comprises a cell (160) and an exogenous material (170).

6. The method of claim 1, wherein a configuration of the CATs (130) is selected from a group comprising lateral to the main channel (120), above the main channel (120), below the main channel (120), and a combination thereof.

7. The method of claim 1, wherein the interfaces (180) comprise a gas-liquid interface, a liquid-liquid interface, a lipid membrane, a polymer membrane, a nano-particle membrane, or a combination thereof.

8. A system (100) for delivery of an exogenous material, the system comprising:

a. a microfluidic platform (110) comprising a main microfluidic channel (120), and one or more cavity acoustic transducers (CATs) (130), wherein the one or more CATs (130) are dead-end channels coupled to the main microfluidic channel (120), wherein the microfluidic platform (110) is coupled to an external acoustic source (140); and b. a fluid (150) disposed through the main microfluidic channel (120), wherein the fluid (150) intersects the CATs (130) to form one or more interfaces (180);

wherein the CATs (130) are configured to oscillate the interfaces (180) to produce a plurality of microstreaming vortices (190) that causes shear-induced mechanical deformation.

9. The system of claim 8, wherein the system (100) additionally comprises an array of electrodes (200), the electrodes interdigitated with the microfluidic platform (110), and wherein the electrodes (200) are configured to promote electroporation (160) when a voltage is applied to the electrodes (200).

10. The system of claim 8, wherein the oscillation is controlled by a piezoelectric transducer (PZT) voltage.

11. The system of claim 8, wherein the CAT (130) is configured to induce pumping of the fluid (150), thereby eliminating the need for external pumping.

12. The system of claim 8, wherein the fluid (150) comprises a cell (160) and the exogenous material.

13. The system of claim 8, wherein a configuration of the CATs (130) is selected from a group comprising lateral to the main channel (120), above the main channel (120), below the main channel (120), and a combination thereof.

14. The system of claim 8, wherein the interfaces (180) comprise a gas-liquid interface, a liquid-liquid interface, a lipid membrane, a polymer membrane, a nano-particle membrane, or a combination thereof.

15. A high-throughput transfection method, comprising:

a. providing a microfluidic platform (110) comprising a main microfluidic channel (120), and one or more cavity acoustic transducers (CATs) (130), wherein the one or more CATs (130) are dead-end channels coupled to the main microfluidic channel (120), wherein the microfluidic platform (110) is coupled to an external acoustic source (140);

b. providing an array of electrodes (200), the electrodes interdigitated with the microfluidic platform (110);

c. flowing a fluid (150) through the main microfluidic channel (120), wherein the fluid (150) intersects the CATs (130) to form one or more interfaces (180);

d. applying acoustic energy to the CATs (130) via the external acoustic source (140) to oscillate the interfaces (180), wherein oscillating the interfaces (180) produces a plurality of microstreaming vortices (190) that causes shear-induced mechanical deformation; and e. applying a voltage to the electrodes (200) so as to achieve electroporation, wherein the electrodes are capable of at least a first mode and a second mode, wherein the first mode achieves generation of pores and the second mode achieves widening of said pores generated in the first mode.

16. The method of claim 15, wherein the oscillation is controlled by a piezoelectric transducer (PZT) voltage.

17. The method of claim 15, wherein the CAT (130) induces pumping of the fluid (150), thereby eliminating the need for external pumping.

18. The method of claim 15, wherein the fluid (150) comprises a cell (160) and an exogenous material.

19. The method of claim 15, wherein a configuration of the CATs (130) is selected from a group comprising lateral to the main channel (120), above the main channel (120), below the main channel (120), and a combination thereof.

20. The method of claim 15, wherein the interfaces (180) comprise a gas-liquid interface, a liquid-liquid interface, a polymer membrane, a nano-particle membrane, or a combination thereof.

* * * * *